(12) United States Patent
Luo

(10) Patent No.: US 12,263,302 B1
(45) Date of Patent: Apr. 1, 2025

(54) HEATABLE AIR DELIVERY TUBE

(71) Applicant: DCSTAR INC, New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 18/416,118

(22) Filed: Jan. 18, 2024

(51) Int. Cl.
 A61M 16/00 (2006.01)
 A61M 16/10 (2006.01)
 A61M 39/08 (2006.01)

(52) U.S. Cl.
 CPC .... A61M 16/0003 (2014.02); A61M 16/0066 (2013.01); A61M 16/1075 (2013.01); A61M 39/08 (2013.01); A61M 2205/0216 (2013.01); A61M 2205/07 (2013.01); A61M 2205/3327 (2013.01); A61M 2205/3368 (2013.01)

(58) Field of Classification Search
 CPC .......... A61M 16/0816; A61M 16/0875; A61M 16/1075–1095; A61M 2205/3368; A61M 16/08–0891; A61M 39/08–18; A61M 16/06–0694; A61M 16/0003; A61M 2205/36; F16L 11/127
 See application file for complete search history.

(56) References Cited

U.S. PATENT DOCUMENTS

| | | | | |
|---|---|---|---|---|
| 2018/0311457 | A1* | 11/2018 | Kavermann | A61M 16/0875 |
| 2021/0379319 | A1* | 12/2021 | Chan | A61M 16/16 |
| 2022/0023581 | A1* | 1/2022 | Bath | A61M 16/0816 |
| 2024/0030661 | A1* | 1/2024 | Beckstein | H01R 13/665 |
| 2024/0139459 | A1* | 5/2024 | O'Connor | A61M 16/022 |

FOREIGN PATENT DOCUMENTS

CN 116637263 A * 8/2023 ........ A61M 16/0816

OTHER PUBLICATIONS

Machine Translation of CN116637263A (Year: 2023).*

* cited by examiner

*Primary Examiner* — Kendra D Carter
*Assistant Examiner* — Mautin I Ashimiu
(74) *Attorney, Agent, or Firm* — Birch, Stewart, Kolasch & Birch, LLP

(57) ABSTRACT

A heatable air delivery tube that maintains the temperature within the tube includes a patient interface end, an airflow generator end, and a heated spiral tube with metal wires that connects the two ends. The patient interface end includes a notch that allows for deformation to better achieve a seal when connected to other tubular connectors. The airflow generator end has a deformable connecting clamp, which allows for self-deformation to secure a snap-fit connection with the airflow generator. The inner diameters of the connectors of both the patient interface end and the airflow generator end are no larger than the tubular connectors they connect to, to ensure a better seal.

17 Claims, 20 Drawing Sheets

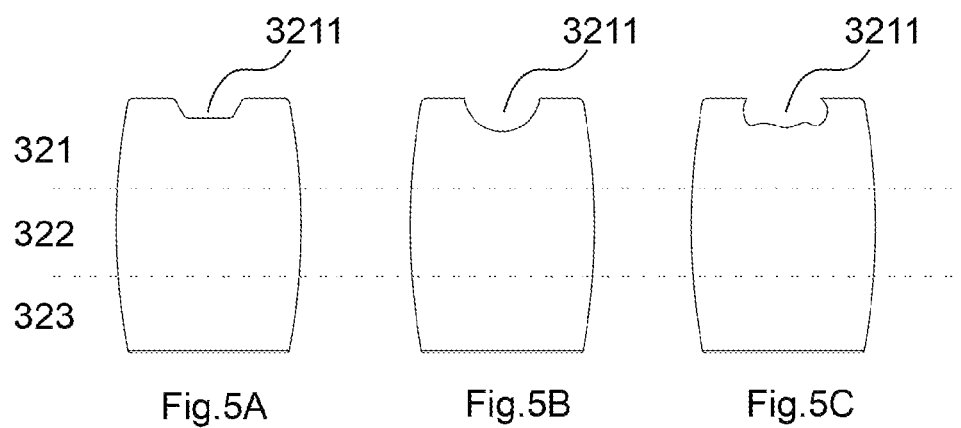

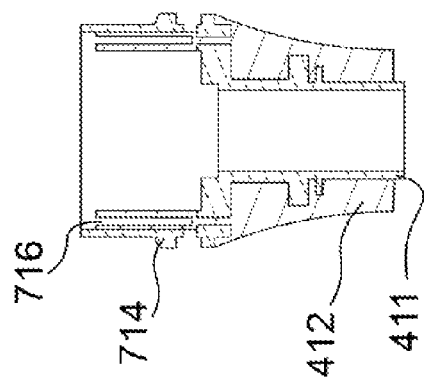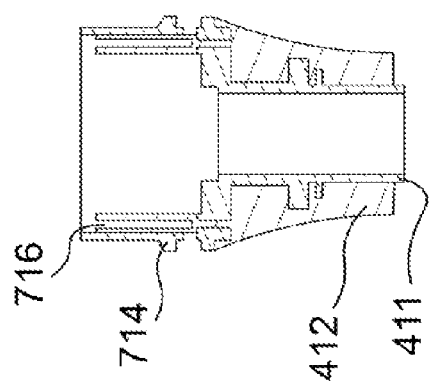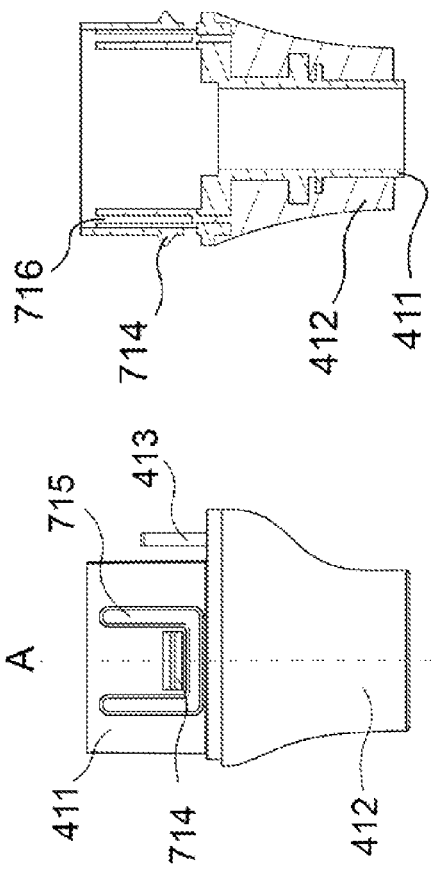

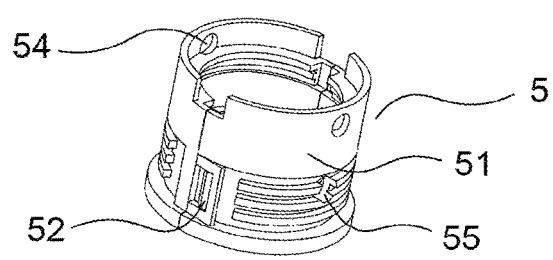
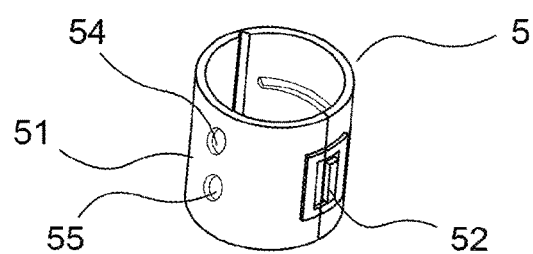
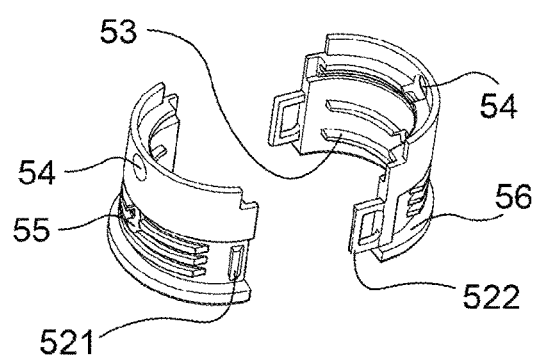
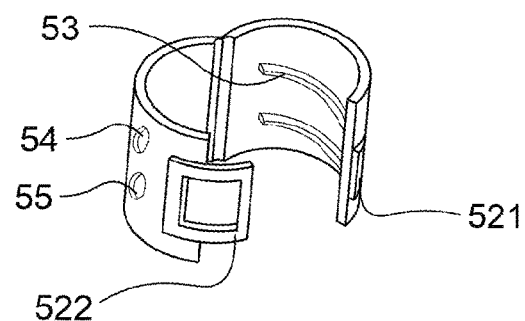
Fig.13A          Fig.13B

HEATABLE AIR DELIVERY TUBE

TECHNICAL FIELD

The disclosure pertains to tubes for the delivery of pressurized gas in ventilatory devices, specifically, the tube of the disclosure relates to a universal modular design.

BACKGROUND

The factors causing sleep apnea are diverse and multifaceted. For example, aging, the misuse of alcohol and drugs, can lead to the relaxation of upper airway muscles, the narrowing or closure of the airway. Obesity can bring an accumulation of extra fat in the neck or throat, which compresses the airway. This often leads to either partial or complete obstruction of the upper airway, and airway narrowing due to structural abnormalities in the nasopharynx. All these conditions can lead to temporary pauses in breathing. Sleep apnea not only disrupts sleep, leading to daytime fatigue, but it can also bring serious health issues, including heart disease, hypertension, cardiovascular problems, metabolic syndrome, and liver problems. The treatment for sleep apnea varies depending on the severity of the condition and individual characteristics. For instance, mild sleep apnea can be managed by lifestyle changes, while moderate to severe cases may require positive airway pressure therapy for effective symptom relief. In cases of severe sleep apnea, surgical intervention may be necessary. Nowadays, many patients opt for the comfort and effectiveness of positive airway pressure therapy.

Positive airway pressure therapy provides pressurized breathable gas into the patient's airway through an airflow generator to lift or open the patient's closed airway for treatment. This therapy typically involves an airflow generator, a liquid storage chamber, an air delivery tube, a patient interface, and a data monitor. The air delivery tube and the liquid storage chamber are crucial components in positive airway pressure therapy, ensuring the feasibility and comfort of the treatment. The air delivery tube provides a connection platform for the whole device, connecting the patient to the machine, while the liquid storage chamber moistens and heats the pressurized gas for the entire device, ensuring the comfort of the treatment. This design helps prevent the delivery of dry, pressurized gas over extended periods to the patient's oral and nasal airways, which could otherwise lead to dryness and discomfort in the mouth, throat, and nasal mucosa, irritate the respiratory tract mucosa, cause inflammatory responses, or make respiratory secretions thicker, thereby increasing the burden on the throat and reducing patient compliance with the treatment. However, the air delivery tube often has a longer length to meet user needs. Due to the external environment or the length of the tube, the pressurized airflow carrying water vapor may condense and adhere to the inner walls of the tube when the airflow passes through the tube, failing to achieve the intended purpose. Moreover, the tube must be sealed to ensure that the gas does not leak during transmission, thereby maintaining the effectiveness of positive airway pressure therapy, which is closely related to the design of the connection ports of the patient assembly and the airflow generator. The connection ports can be divided into one end connecting to the patient assembly and the other end connecting to the airflow generator, both requiring common needs in sealing, ease of use, low noise and adaptability. The connection junction of the elbow in most patient assemblies on the market is typically 15 mm or 22 mm in diameter. Therefore, the model of the end of the air delivery tube that contacts the patient assembly is usually the same. However, the inner diameter of the end is often slightly larger than the outer diameter of the elbow in the patient assembly. This design facilitates a smooth connection between the elbow and the air delivery tube. Nonetheless, the end is usually made of a flexible material, which, due to the frequent installation and removal required by the device, is prone to fatigue deformation or material aging, gradually losing its sealability. As for the end connecting to the airflow generator, there can be variations due to different brands' machine designs, making it challenging to achieve a universal design for this component. Consequently, users need to purchase specific models of tubes to connect the patient components with the airflow generator.

Therefore, there is a need to design an air delivery tube that is comfortable, adaptable, and sealed. Metal wires should be placed along the path through which the gas flows in the air delivery tube to ensure that the space inside the tube can maintain a certain temperature during the transmission of gas. Moreover, the structural design of the end that contacts the patient assembly should be optimized to extend the lifespan of the connector. Furthermore, the end that connects to the airflow generator should have a modular design to enable compatibility with different models of machines, enhancing the overall flexibility of the air delivery tube. This design aims to provide patients with a more convenient user experience and a wider range of options.

SUMMARY

Based on the aforementioned shortcomings of existing air delivery tubes, a heatable air delivery tube that is comfortable, adaptable, and sealed is provided in the disclosure.

A heatable air delivery tube is configured to form a connection with an airflow generator and a patient interface assembly, and to deliver pressurized breathable gas to an airway of a patient, the air delivery tube including at least some of the following elements or features.

A patient interface end includes a bracket, an elastomer, and a clip. The bracket is configured to connect to a heated spiral tube, the elastomer is configured to connect to the patient interface assembly, and the clip is configured to secure the heated spiral tube. The bracket includes a cavity to place a thermistor and includes a positioner in contact with the clip, with the elastomer having an upper end, a lower end, and a middle part. The upper end includes at least one notch, the lower end is configured to connect to the clip, and there is a non-uniform thickness from the upper end to the lower end.

The thermistor is placed within the cavity of the bracket at the patient interface end, to detect the temperature of gas within the air delivery tube.

The heated spiral tube, configured to connect to the patient interface end at one end and to an airflow generator end at an other end, includes metal wires, a compressible flexible wall, and a spring-like coil, together to form the compressible heated spiral tube.

The airflow generator end, configured to connect to the heated spiral tube, includes a sealing element in contact with the airflow generator, a support element to position the airflow generator, the clip to secure the heated spiral tube, and an electrical connector.

The notch at the upper end of the elastomer of the patient interface end does not exceed half a length of the elastomer, and a middle part of the elastomer of the patient interface end is thicker than both the upper end and the lower end of the elastomer.

In one embodiment, the patient interface end is connectable to a tubular connector, an inner diameter of the upper end of the elastomer of the patient interface end is smaller than or equal to an outer diameter of an elbow or the tubular connector.

In one embodiment, the positioner on the bracket at the patient interface end is a protrusion, a groove, or a magnet.

In one embodiment, a gripping portion is provided on the elastomer of the patient interface end.

In another embodiment, a heatable air delivery tube is disclosed herein, configured to form a connection with an airflow generator and a patient interface assembly, and to deliver pressurized breathable gas to an airway of a patient, the air delivery tube including at least some of the following elements or features.

An airflow generator end includes a support element, a sealing element, a clip, and an electrical connector. The support element and the sealing element are partially in contact with the airflow generator, and the support element is interconnected to the sealing element. The clip is configured to secure the heated spiral tube, the electrical connector is configured to connect to the airflow generator to form a continuous circuit. The support element includes a first end and a second end, and the first end is internally connectable to the sealing element and includes a connecting clamp with a wall thickness no greater than the wall thickness of other parts. And the connecting clamp includes a gap and a guiding slanted protrusion, configured to be deformably fixed to the airflow generator. The second end is externally connectable to the heated spiral tube and the clip, and the second end includes a positioner in contact with the clip. The sealing element includes a third end and a fourth end, with the third end including a clearance at a position corresponding to the connecting clamp and having an inner diameter not exceeding an outer diameter of an air supply tube of the airflow generator, and the third end is configured to seal the airflow generator while the fourth end is configured to provide a gripping portion.

The heated spiral tube, configured to connect to the patient interface end at one end and to the airflow generator end at an other end, includes metal wires, a compressible flexible wall, and a spring-like coil, together to form the compressible heated spiral tube.

The patient interface end, configured to connect to the heated spiral tube, includes an elastomer to connect to the patient interface assembly, a bracket to connect to the heated spiral tube, and the clip to secure the heated spiral tube.

In one embodiment, the third end of the sealing element of the airflow generator end is partially recessed to form a height difference or a groove with a surface of the first end of the support element.

In one embodiment, a sealing ring is provided between the third end and the fourth end of the sealing element of the airflow generator end.

In one embodiment, a gripping portion is provided on the fourth end of the sealing element of the airflow generator end, with the gripping portion forming a height difference with a surface of the fourth end.

In one embodiment, the support element at the airflow generator end includes an opening to accommodate the electrical connector, surrounded by a channel to house a silicone ring, with the electrical connector being larger than the opening.

In yet another embodiment, a heatable air delivery tube is disclosed herein, configured to form a connection with an airflow generator and a patient interface assembly, and to deliver pressurized breathable gas to an airway of a patient, the air delivery tube including at least some of the following elements or features.

A patient interface end, configured to connect to a heated spiral tube, includes an elastomer to connect to the patient interface assembly, a bracket to connect to the heated spiral tube, and a clip to secure the heated spiral tube, wherein the bracket includes a positioner.

An airflow generator end, configured to connect to the heated spiral tube, includes a sealing element in contact with the airflow generator, a support element to position the airflow generator, a clip to secure the heated spiral tube, and an electrical connector, wherein the support element includes another positioner;

The heated spiral tube, configured to connect to the patient interface end at one end and with the airflow generator end at an other end, includes metal wires, a compressible flexible wall, and a spring-like coil, together to form the compressible heated spiral tube.

The clip includes a separable annular wall, at least one pair of matching male buckle and female buckle, an anti-overflow surface, a positioning receptacle, with the annular wall being externally configured to contact the elastomer of the patient interface end or the sealing element of the airflow generator, the annular wall including an internal protruding piece, configured to limit displacement of the heated spiral tube. The male buckle includes a slanted surface to guide deformation of the female buckle, an inner edge circumference of the female buckle is larger than an outer edge circumference of the male buckle, and the positioning receptacle includes a form corresponding to the positioner, configured to contact and limit movement of the clip.

In one embodiment, the anti-overflow surface includes an outer diameter greater than an outer diameter of the annular wall, configured to contact and prevent downward overflow of the elastomer of the patient interface end or the sealing element of the airflow generator.

In one embodiment, a separable form of the annular wall of the clip is either a one-piece with a connection or two completely separated parts, with the annular wall being evenly divided in half or being separated from a one-third point.

In one embodiment, the protruding piece of the annular wall of the clip is non-continuous, either provided with a slope that complies with spiral threads or being flat.

In one embodiment, an exterior of the annular wall of the clip is partially concave and convex, and the annular wall includes at least one inlet for overmolding materials.

In another embodiment, a heatable air delivery tube is disclosed herein, configured to form a connection with an airflow generator and a patient interface assembly, and to deliver pressurized breathable gas to an airway of a patient, the air delivery tube including at least some of the following elements or features.

A patient interface end, configured to connect to a heated spiral tube includes an elastomer to connect to the patient interface assembly, a bracket to connect to the heated spiral tube, and a clip to secure the heated spiral tube.

An airflow generator end includes a first part connectable to the heated spiral tube and a second part connectable to the first part, with the second part being configured to seal the airflow generator. The first part includes a support element, a sealing element, a clip, a connecting portion, and an electrical connector, with the clip being configured to secure the heated spiral tube, and the electrical connector configured to connect to an electrical connector of the second part to form a continuous circuit. The support element is configured to connect to the heated spiral tube and the clip, and includes a positioner in contact with the clip. And the second part is deformably fixed to the airflow generator, including a shell, soft rubber, a corresponding portion, and the electrical connector. The soft rubber includes a hollow section for accommodating an air supply tube of the airflow generator, the electrical connector of the second part connects to an electrical connector of the first part to form a continuous circuit, and the first part and the second part are connectable through the connecting portion and the corresponding portion.

The heated spiral tube, configured to connect to the patient interface end at one end and to the airflow generator end at the other end, includes metal wires, a compressible flexible wall, and a spring-like coil, together to form the compressible heated spiral tube.

In one embodiment, the first part of the airflow generator is secured to the heated spiral tube, the first part and the second part are connectable through the connecting portion and the corresponding portion, and the first part and the second part are connectable by one or more detachable or undetachable methods: snap-fit, magnetic attraction, rotation, or ultrasonic.

In one embodiment, the second part of the airflow generator is provided with different forms as needed.

In one embodiment, the electrical connector of the first part and the electrical connector of the second part are either slot-type or contact-type.

In yet another embodiment, a heatable air delivery tube is disclosed herein, configured to form a connection with an airflow generator and a patient interface assembly, and to deliver pressurized breathable gas to an airway of a patient, the air delivery tube including at least some of the following elements or features.

An airflow generator end includes a support element, a sealing element, a clip, and an electrical connector. The support element and the sealing element are partially in contact with the airflow generator, and the support element is interconnected to the sealing element. The clip is configured to secure the heated spiral tube, the electrical connector is configured to connect to the airflow generator to form a continuous circuit. The support element includes a first end and a second end, and the first end is internally connectable to the sealing element and includes a connecting clamp with a wall thickness no greater than the wall thickness of other parts, configured to be deformably fixed to the airflow generator, while the second end is configured to connect to the heated spiral tube and the clip. The sealing element includes a third end and a fourth end, with the third end being configured to seal the airflow generator and the fourth end configured to provide a gripping portion.

The patient interface end, configured to connect to the heated spiral tube, includes an elastomer to connect to the patient interface assembly, a bracket to connect to the heated spiral tube, and the clip to secure the heated spiral tube. And an inner diameter of the patient interface end is not greater than an outer diameter of an elbow.

The clip includes an annular wall that is externally configured to contact the elastomer of the patient interface end or the sealing element of the airflow generator, at least one pair of matching male buckle and female buckle, and an anti-overflow surface with an outer diameter greater than an outer diameter of the annular wall.

The heated spiral tube includes metal wires, configured to connect to the patient interface end at one end and to the airflow generator end at an other end.

In one embodiment, the third end of the sealing element of the airflow generator end is partially recessed to form a height difference or a groove with a surface of the first end of the support element.

In one embodiment, a separable form of the annular wall of the clip is either a one-piece with a connection or two completely separated parts, with the annular wall being evenly divided in half or being separated from a one-third point.

In one embodiment, an internal protruding piece provided on the annular wall of the clip is non-continuous, either provided with a slope that complies with spiral threads or being flat, and an exterior of the annular wall of the clip is partially concave and convex, with the annular wall including at least one inlet for overmolding materials.

The benefits of a heatable air delivery tube provided by the disclosure can at least include:

1) The heatable air delivery tube provided by this disclosure incorporates a notch design. On the market, the end of most air delivery tubes that connect to an elbow usually has an inner diameter slightly larger than the outer diameter of the elbow. This design aims to ensure that the elbow can smoothly connect to the air delivery tube. The end that connects to the elbow, considering its need for sealability and tactile feel, is typically made from flexible materials like silicone, rubber, or thermoplastic elastomers. However, due to the frequent installation and removal required by the device, the flexible materials are prone to fatigue deformation or material aging from repeated stress loading and unloading. This results in a gradual loss of their original shape and elasticity, eventually leading to a failure of the sealing effect and an increased likelihood of slippage. To maintain the function of a smooth connection between the elbow and the air delivery tube and to extend the lifespan of the end that connects to the elbow, a notch is set at the upper end of the elastomer of the patient interface end. Additionally, the inner diameter of the elastomer is configured to be less than or equal to the outer diameter of the tube openings connected with the elastomer. a) The notch at the upper end of the elastomer provides a flexible structure, increasing the operability and adaptability of the elastomer. The upper end of the elastomer can be supported to deform into a broader aperture at the notch, allowing the lower end of the elbow or other tube openings to enter smoothly. b) The inner diameter of the elastomer being less than or equal to the outer diameter of the tube openings connected with the elastomer provides a tighter seal. Meanwhile, when the elastomer undergoes fatigue deformation, an elastomer with an inner diameter slightly larger than the outer diameter of the elbow will have an extended lifespan and avoid loosening after aging.

2) The heatable air delivery tube provided by this disclosure has a modular design for the airflow generator end. There are many well-known ventilators on the market, and different brands of ventilators have variations in their components. For the end of the air delivery tube that connects to the elbow, due to regulatory requirements, most on the market have connectors with a diameter of 15 mm or 22 mm. However, for the end that connects to the airflow generator, there are differences due to the brands' machine designs, making it difficult to achieve a universal design for the components. The modular design of the airflow generator end of the air delivery tube: the part that connects to the heated spiral tube only needs to meet the requirement of connecting to the heated spiral tube, so this part is configured as a universal base (a first part). The part that connects to different machines only needs to have a shape that is compatible with the machine and have positions for placing the electrical connectors. The base and the changeable upper part (a second part) can be connected through simple methods like snap-fit, rotation, ultrasonic, etc. Electrical connectors, can form a continuous circuit through slot-type or contact-type connections. When the base and the changeable upper part are configured separately, the base's fixed connection with the heated spiral tube is more complex compared to the upper part's connection with the machine. With a universal base, the upper part model that connects to the machine can be configured and manufactured more simply. By changing the adaptability of the upper part, the effect of matching different machine models can be achieved. This modular design provides at least three benefits: a) For manufacturing and design, modular design reduces the burden of production and assembly, improves the product's customizability which means that with a universal base, the upper part can be configured to match different machines and meet the needs of different machines as a whole. This design also helps speed up development and production, and reduces costs and the repetition of design and manufacturing work by mass-producing the same base part. Moreover, such a feature focuses on controlling modular components rather than the whole during production, further reducing the overall scrap rate, and saving production costs. b) For product quality, modular design supports individual testing and verification, improving quality control, and enables the introduction of new technologies by replacing or upgrading individual modules, allowing gradual upgrades to meet or adapt to new technologies or standards without affecting the overall system. c) For storage costs, modular design reduces the overall number of products in storage, requiring only the storage of necessary modules or components. In this way, the warehouse space can be more effectively utilized and the corresponding module inventory can be adjusted according to market demand, reducing the occurrence of insufficient inventory or overpurchasing and backlog due to fluctuations in demand. d) For the environment, air delivery tubes typically contain plastic materials like polyethylene and polycarbonate, whose production involves the use of fossil fuels, consuming large amounts of oil and natural gas, non-renewable resources, and emitting greenhouse gases. After use, plastic products are not easily degradable and can accumulate in the environment, causing pollution. Modular design improves the overall flexibility of the product, and during the maintenance process, only the relevant module parts rather than the entire product need to be replaced. This not only reduces maintenance costs but also allows damaged modules to be recycled or upgraded for research, reducing waste, resource consumption, and energy use, making it more environmentally friendly.

3) The heatable air delivery tube provided by this disclosure includes a universal design for the clip. The air delivery tube 1 includes two connection junctions with the heated spiral tube 2, where the heated spiral tube 2 is secured at both ends using the clip 5 and then overmolded. This ensures a more stable connection and extends the overall lifespan of the tube. Since the functions realized by the two ends of the air delivery tube when connected to other external components are different, their structural designs also slightly vary. However, the part that connects to the heated spiral tube can be configured to be substantially the same, achieving a universal design for the clip. The extensive use of the clip in a product contributes to reducing research and development costs as well as production costs. The research and development phase can be as simple as designing and verifying that the connection at one end is reasonable and stable, reducing the additional costs associated with constant modification and customization.

4) The heatable air delivery tube provided by this disclosure has a unique connection method of the heated spiral tube. To ensure the stability of the connection between the heated spiral tube and the airflow generator end and the patient interface end, the connection between the heated spiral tube and the two ends is achieved through a clip. Firstly, the parts at both ends that contact the heated spiral tube have a positioner and a sufficient contact surface in contact with the heated spiral tube. The positioner provides positioning for the clip to prevent it from moving, and the sufficient contact surface provides a force area for the heated spiral tube, increasing friction between the heated spiral tube and the two ends. Secondly, the clip has a positioning receptacle and an internal protruding piece. The positioning receptacle works with the positioner at both ends, and the internal protruding piece intrudes into the space of the spiral tube, limiting displacement of the heated spiral tube. This setup achieves the first fixation among the heated spiral tube, the airflow generator end and the patient interface end. Finally, by molding, materials like silicone with good deformation capability are injected into the space between the heated spiral tube, the airflow generator end and the patient interface end, enhancing the friction in the connection and achieving a second fixation, ultimately better securing the whole assembly.

5) The heatable air delivery tube provided by this disclosure has a specifically designed connecting clamp at the airflow generator end. The connection to the airflow generator is mechanically fixed. To achieve user-friendliness, the wall thickness of the connecting clamp is configured to be no greater than the wall thickness of other parts, allowing the connecting clamp to have elastic arms that can deform. A guiding slanted surface is set on the connecting clamp, enabling the airflow generator end to autonomously deform upon entering the connection port of the machine and to secure to the airflow generator. Simultaneously, the reverse slanted surface guides the elastic arms to deform for separation, making the product easier for users to handle.

6) The heatable air delivery tube provided by this disclosure presents a recessed design of the sealing element of the airflow generator end. Due to the inflexibility in size of the machine and the specificity of the user group, connecting the airflow generator end can be challenging because of the blind spot in the field of vision, making it difficult for the user to locate the interface between the end and the machine. By designing the interior of the connection junction to be recessed, creating a height difference with the end surface of the connection junction to form a groove, this allows the product to have a positioning function when it interfaces with the machine through the groove, aiding the particular user group in achieving easier connections.

BRIEF DESCRIPTION OF THE DRAWINGS

FIGS. 5A, 5B and 5C are schematic diagrams of different forms of a notch at the upper end of a patient interface end in accordance with an embodiment;

FIGS. 8A, 8B and 8C are cross-sectional views taken along line A-A;

FIGS. 13A and 13B are schematic diagrams of the structure of a clip in accordance with an embodiment;

DETAILED DESCRIPTION

Figure 1:
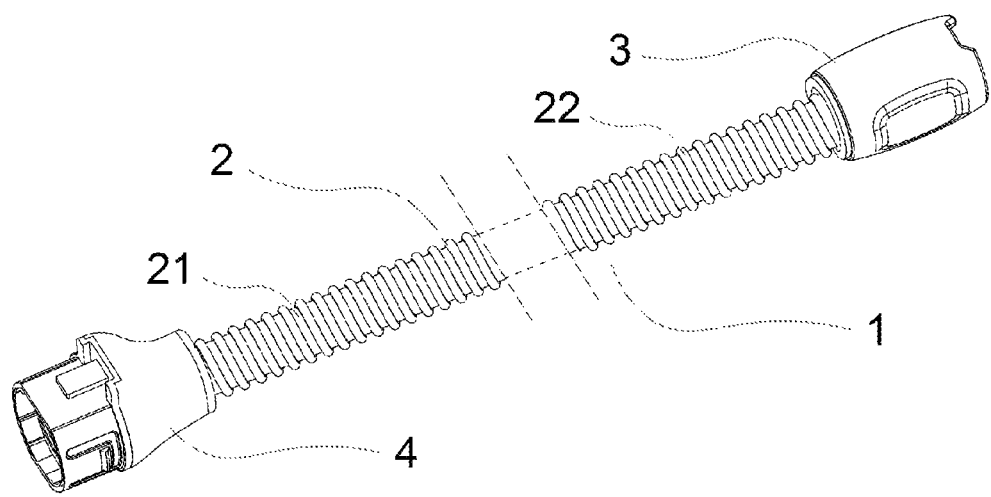
FIG. 1 is a structural schematic diagram of an air delivery tube in accordance with an embodiment.

To make the objectives, features, and advantages of the disclosure more clear and understandable, a detailed explanation of the specific embodiments of the disclosure is provided in conjunction with the accompanying drawings. Many specific details are set forth in the following description to facilitate a full understanding of the disclosure. However, it should be understood that the disclosure can be implemented in many different ways other than those described here, and those skilled in the relevant field can make similar improvements without departing from the spirit of the disclosure. Therefore, the disclosure is not limited by the specific embodiments disclosed below.

Unless otherwise defined, all technical and scientific terms used herein have the same meaning as commonly understood by one of ordinary skill in the art to which the disclosure belongs. The terms used in this specification are for the purpose of describing particular embodiments only rather than limiting the disclosure.

The disclosure integrates the concepts of modularity and component universality (where components can be used in different positions within the same product) into the design of the air delivery tube. It also redesigns the two ends that connect to the patient assembly and to the airflow generator, as well as the method by which the middle tube connects to these ends. This design ensures ease of use and a secure seal while extending the overall lifespan of the product. The air delivery tube 1 is configured to include three parts: a patient interface end 3, an airflow generator end 4, and a heated spiral tube 2. The patient interface end 3 is configured to connect to an elbow or a short tube in the patient assembly, the airflow generator end 4 is configured to connect to the air supply tube of the airflow generator, and the heated spiral tube 2 is configured to connect to the patient interface end 3 at one end and to the airflow generator end 4 at the other end. To prevent water vapor condensation, the heated spiral tube 2 includes three or more metal wires of the same diameter. Depending on temperature requirements, the diameter of the metal wire cross-section can be changed or different materials can be used to obtain varying resistances and thus produce different amounts of heat. To make the air delivery tube 1 flexible, a (compressible) deformable flexible wall 21 is used to form a hollow tube. A stretchable and compressible spring-like coil 22 connects to the outer surface of the flexible wall 21, allowing the flexible wall 21 with a certain length to be compressible and more robust (sturdy) and more durable. The heated spiral tube 2 includes metal wires, a compressible flexible wall 21, and a spring-like coil 22, together forming a compressible heated spiral tube 2. The heated spiral tube 2 is connectable to the patient interface end 3 and the airflow generator end 4 through methods such as molding and clips 5, forming a complete air delivery tube 1. The total length of the air delivery tube 1 does not exceed 3000 mm. Through the design of the support element 411 and the bracket 31, some parts have the same connection or surface structure, allowing both ends to connect to the heated spiral tube 2 using the same connection method.

Detailed embodiments are presented below to elucidate several structures of a heatable air delivery tube 1.

Embodiment 1

In this embodiment, a heatable air delivery tube 1 includes three parts: a patient interface end 3, an airflow generator end 4, and a heated spiral tube 2, configured to form a connection with an airflow generator and a patient interface assembly, and to deliver pressurized breathable gas to the airway of a patient. As shown in FIG. 1, the patient interface end 3 is configured to connect to an elbow or a short tube in the patient assembly, and the airflow generator end 4 is configured to connect to the air supply tube of the airflow generator, meaning the heated spiral tube 2 connects to the patient interface end 3 at one end and to the airflow generator end 4 at the other end.

Figure 2:
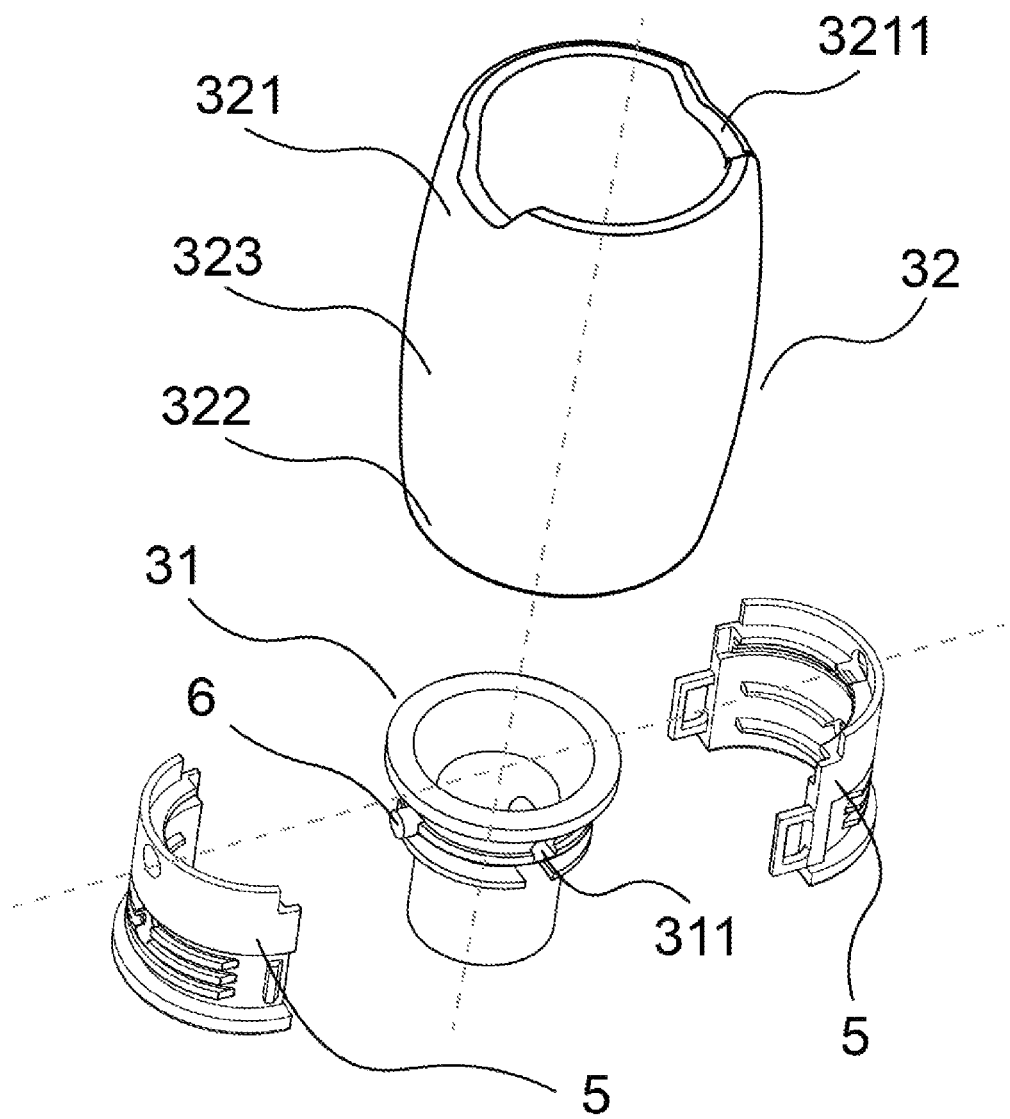
FIG. 2 is a structural exploded view of a patient interface end of an air delivery tube in accordance with an embodiment.
Figure 4C:
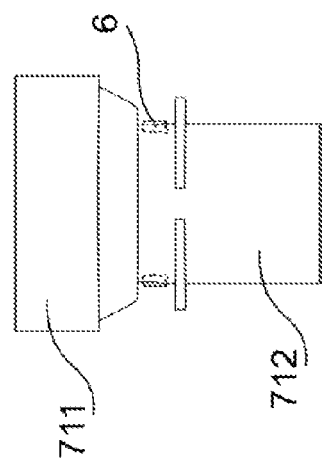
FIGS. 4A, 4B and 4C are schematic diagrams of different forms of a positioner in accordance with an embodiment.
Figure 4B:
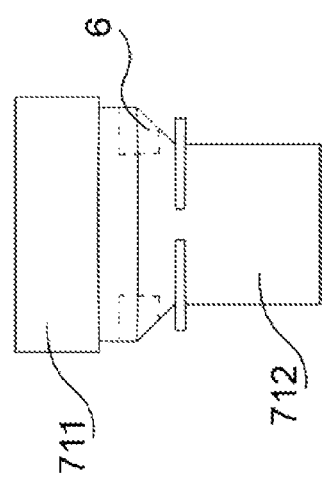
Figure 4A:
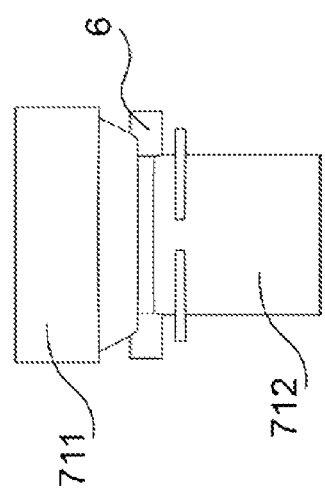
Figures 6A, 6B, 6C:
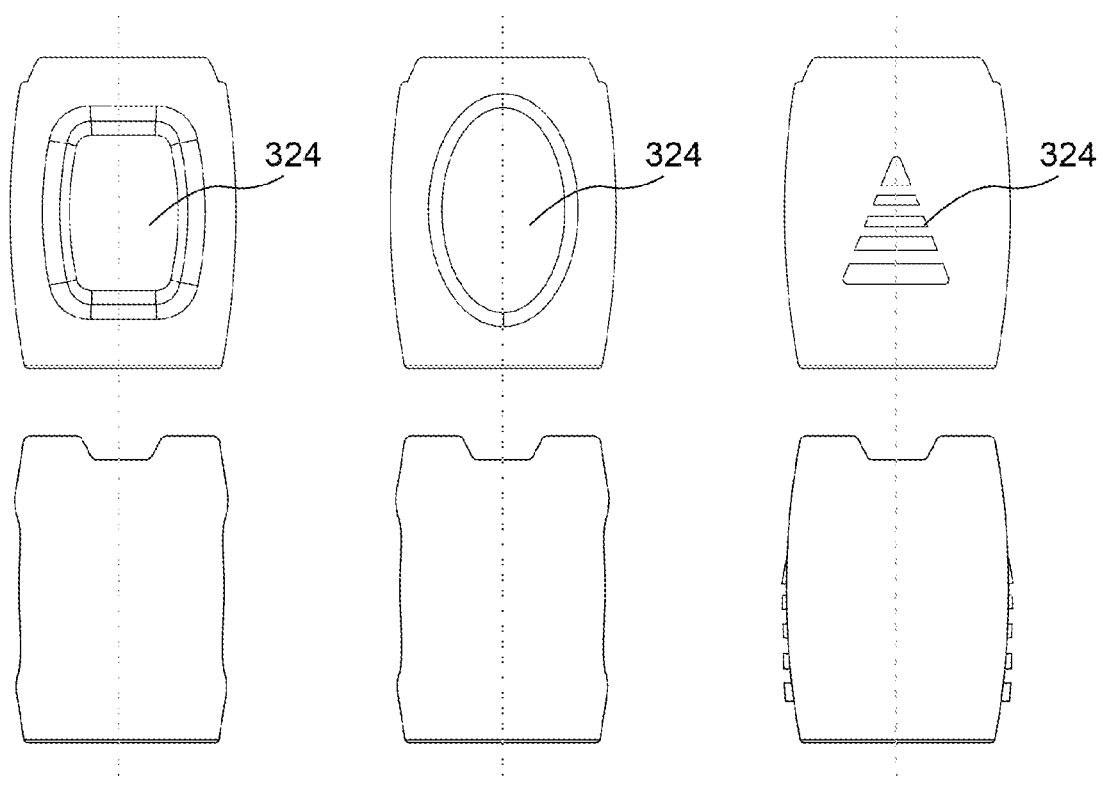
FIGS. 6A, 6B and 6C are schematic diagrams of different forms of a gripping portion on the surface of the elastomer of a patient interface end in accordance with an embodiment.

As depicted in FIG. 2, specifically, the patient interface end 3 includes a bracket 31, an elastomer 32, a thermistor 33, and a clip 5 to secure the heated spiral tube 2. The patient interface end 3 is configured to connect to tubular connectors (e.g., an elbow). The wall of the bracket 31 forms a cylindrical through-channel in the middle, with a minimum inner diameter of no less than 10 mm to ensure smooth passage of pressurized airflow. The bracket 31 is configured to connect to the heated spiral tube 2. Part of the wall of the bracket 31 forms a contact surface to connect to the heated spiral tube 2, roughly about at or between 300 to 1350 mm$^2$ in size, ensuring enough area is provided for a stable connection between the heated spiral tube 2 and the bracket 31, avoiding an unstable connection due to an overly small contact surface. The wall of the bracket 31 has a positioner 6 configured to contact the clip 5, and a cavity 311 to place a thermistor 33. As shown in FIG. 4, specifically, the positioner 6 can be a protrusion, a groove, a magnet, or other forms compatible with the clip 5. The length of a protruding or grooved positioner 6 is approximately at or between 1 to 8 mm, with a cross-sectional shape that can be annular, square, triangular, etc. The material of the positioner 6 can be the same as the wall of the bracket 31, or different materials like silicone, acrylic, etc. The thermistor 33 is placed within the cavity 311 to detect the temperature of the gas in the air delivery tube. The cavity 311 can be an extension from the wall of the bracket 31 towards the central axis of the cylinder, or an external component connectable to the wall of the bracket 31 through molding, ultrasonic, etc. The top of the cavity 311 can extend beyond the central axis of the cylinder to ensure effective contact of the thermistor 33 with the airflow in the tube for temperature detection. The material of the cavity 311 can be the same as the wall of the bracket 31 or different materials like silicone, acrylic, metal, etc. The bracket 31 can be made from rigid materials such as polyethylene, polypropylene, polycarbonate, etc. Part of the wall of the bracket 31 also contacts the elastomer 32. The bracket 31, one end of the heated spiral tube 2, and the clip 5 form a tight connection by connecting with the elastomer 32. The elastomer 32 has an upper end 321 configured to connect to the tubular connector in the patient assembly, a lower end 322 (configured to be in close contact with the clip 5, the bracket 31, the heated spiral tube 2) and a middle part 323 connecting the upper end 321 and lower end 322. The interior of the upper end 321 is hollow cylindrical, approximately at or between 15 to 30 mm in length to ensure sufficient length for a stable connection with the elbow, and about at or between 10 to 22 mm in its inner diameter, smaller than or equal to the outer diameter of the connection junction of the elbow or the tubular connector in the patient assembly, which means the inner diameter of the patient interface end 3 is not greater than the outer diameter of the elbow, ensuring complete sealing of the connection junction of the elbow or the tubular connector, thereby preventing gas leakage. As shown in FIG. 5, specifically, the upper end 321 has at least one notch 3211, the contour shape of which can be trapezoidal, arc-shaped, etc. The notch 3211 provides a flexible structure to the upper end 321, enhancing the deformability of the elastomer 32, making it easier for the upper end 321 to deform at the notch 3211 into a broader aperture to connect to the elbow. The length of the notch 3211 in the upper end 321 does not exceed half the length of the elastomer 32, and the width of the notch 3211 does not exceed half the inner diameter of the upper end 321 of the elastomer 32, preventing the notch 3211 from being too large and reducing the sealing effect of the patient interface end 3. The lower end 322 connects to the clip 5 and fills the space between the clip 5 and the heated spiral tube 2. The length of the lower end 322 is about at or between 10 to 25 mm. The middle part 323 contacts part of the wall of the bracket 31, and the elastomer 32 has a non-uniform thickness from the upper end 321 to the lower end 322, with the middle part 323 being thicker than the upper end 321 and the lower end 322. The middle part 323 has the thickest wall, greater than 2 mm, to increase the hardness of the elastomer 32 and prevent the upper part of the elastomer 32, which lacks the support of the bracket 31, from easily breaking. The overall length of the elastomer 32 is approximately at or between 35 to 70 mm, providing sufficient area for a gripping portion 324 for the user. As shown in FIG. 6, specifically, the outer surface of the elastomer 32 can have a groove or a protrusion to facilitate user grip. The elastomer 32 can be made from materials with good sealing properties and capable of slight deformation, such as silicone or rubber with a hardness of at or between 30 to 70 Shore A, or thermoplastic elastomer with a hardness of at or between 20 to 80 Shore A.

Figure 3:
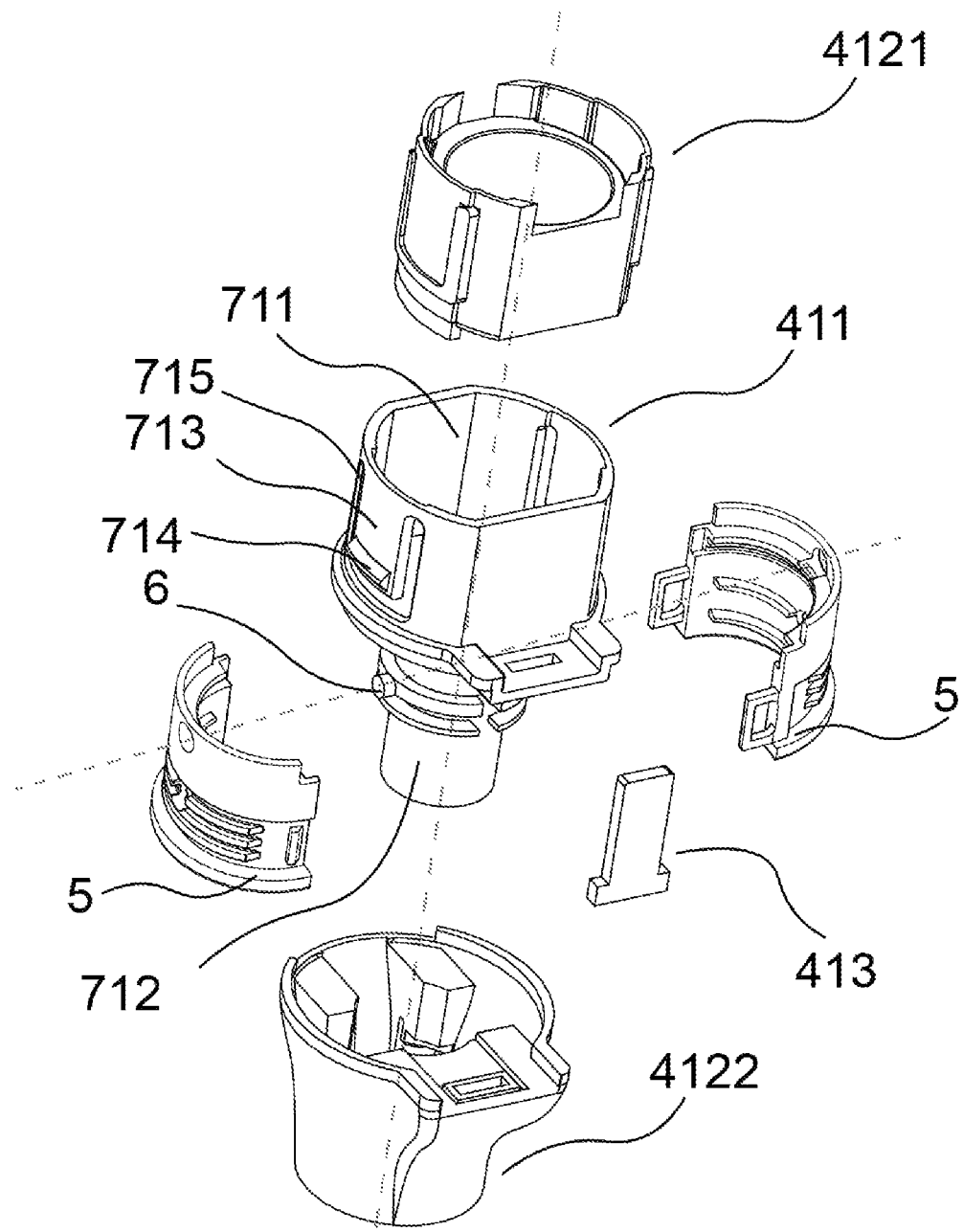
FIG. 3 is a structural exploded view of an airflow generator end of an air delivery tube in accordance with an embodiment.
Figure 7:
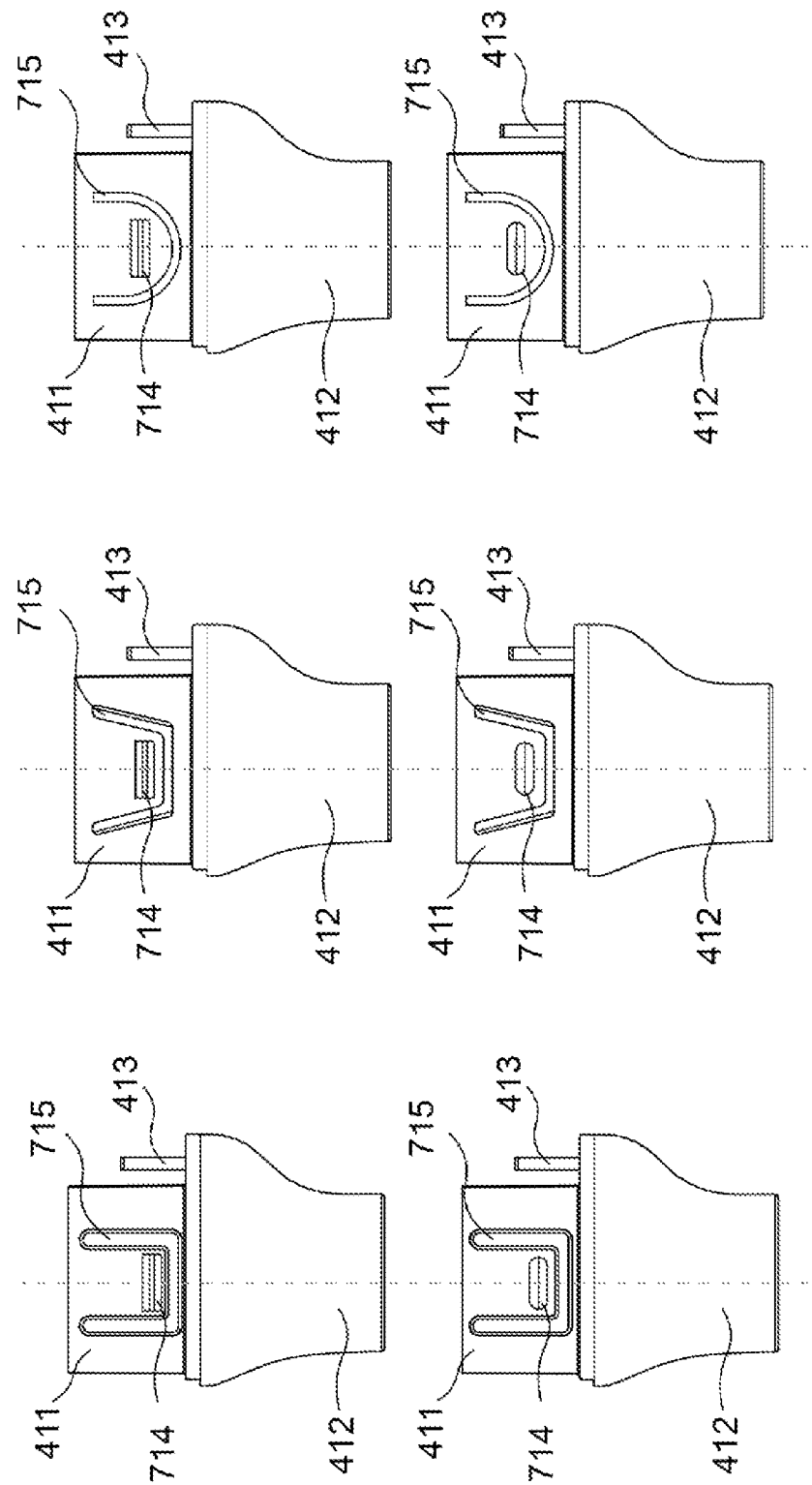
FIG. 7 is a front view of different forms of a gap between the connecting clamp at the airflow generator end in accordance with an embodiment.
Figure 10A:
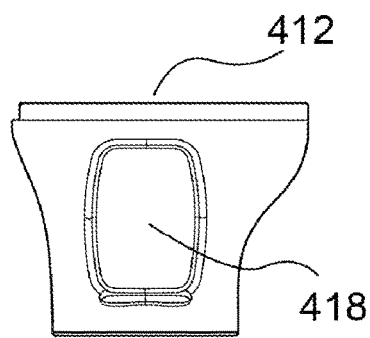
FIGS. 10A, 10B and 10C are schematic diagrams of different forms of a gripping portion on the surface of the sealing element of the airflow generator end in accordance with an embodiment.
Figure 10B:
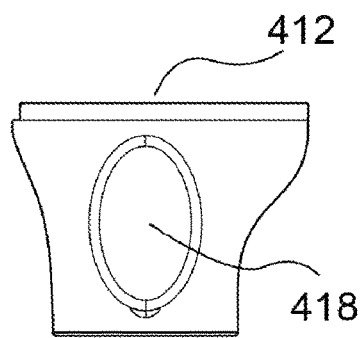
Figure 10C:
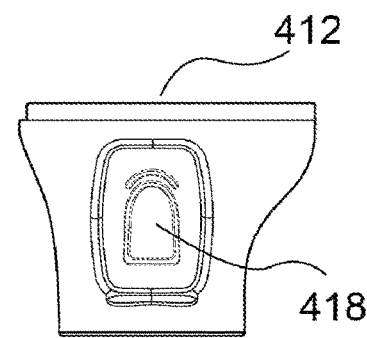

As shown in FIG. 3, specifically, the airflow generator end 4 includes a support element 411 with a first end 711 and a second end 712, a sealing element 412 with a third end 4121 and a fourth end 4122, a clip 5, and an electrical connector 413 (which can deliver electrical current or signals). The overall length of the airflow generator end 4 is about at or between 40 to 60 mm. The support element 411 is configured to position the airflow generator. The bracket 31 incorporates a wall that defines a cylindrical channel within its center, with a minimum inner diameter of no less than 10 mm, ensuring smooth passage of pressurized airflow. The second end 712 is externally connectable to the heated spiral tube 2 and the clip 5. The wall of the second end 712 of the support element 411 forms a contact surface to connect to the heated spiral tube 2, about at or between 300 to 1350 $mm^2$ in size, ensuring enough area is provided for a stable connection between the heated spiral tube 2 and the support element 411, avoiding an unstable connection due to an overly small contact surface. The wall of the support element 411 has a positioner 6 in contact with the clip 5, an outwardly extending platform 415, and a connecting clamp 713. The positioner 6, located on the wall of the second end 712 of the support element 411, can be a protrusion, a groove, a magnet, etc., with a length of approximately between 1 to 8 mm and a cross-sectional shape that can be annular, square, triangular, etc., made from the same material as the wall of the bracket 31 or different materials like silicone, acrylic, etc. The outwardly extending platform 415 is configured to contact the fourth end 4122 of the sealing element 412 on one side and prevent the sealing element 412 from upward overflow and the platform 415 has an opening 416 to house the electrical connector 413. The opening 416 can have a channel to accommodate a silicone ring, stabilizing the electrical connector 413 and preventing liquid from flowing into the space between the silicone and the electrical connector 413. As shown in FIG. 7, specifically, the wall of the support element 411 partially hollows out to form a deformable connecting clamp 713, with a gap 715 not exceeding 5 mm. The wall thickness of the elastic arms of the connecting clamp 713 is configured to be no greater than other parts (excluding the elastic walls of the support element 411), allowing the connecting clamp 713 to be more elastically deformable than the support element 411. As shown in FIG. 8, specifically, the connecting clamp 713 has a guiding slanted surface (a guiding slanted protrusion 714), allowing the airflow generator end 4 to deform autonomously when entering the connection port of the machine and secure to the airflow generator, while the reverse slanted surface guides the elastic arms to deform for separation, facilitating easier use of the product. The electrical connector 413 passes through the opening 416 of the platform 415 of the support element 411 and contacts the platform 415, with the contact region between the electrical connector 413 and the platform 415 being larger than the size of opening 416 to prevent the electrical connector 413 from completely passing through opening 416 and detaching from the airflow generator end 4. The support element 411 can be made from rigid materials such as polyethylene, polypropylene, polycarbonate, etc., with its first end 711 being internally configured to connect to the third end 4121 of the sealing element 412, and the second end 712 configured to connect to the fourth end 4122 of the sealing element 412. The sealing element 412 is in contact with the airflow generator. The third end 4121 of the sealing element 412 includes a portion forming an internal cylindrical passage to accommodate the air delivery tube of the airflow generator, with an inner diameter not greater than the outer diameter of the air supply tube, ensuring a sealed connection between the sealing element 412 and the airflow generator. The third end 4121 has a clearance 716 at the corresponding position of the connecting clamp 713, providing space for deformation of the connecting clamp 713. The top part of the third end 4121 is recessed about between 3 to 10 mm, forming a height difference or a groove with the surface of the first end of the support element 411, thereby preventing users from being unable to quickly locate the interface between the end and the machine due to a blind spot in their field of vision during connection. The fourth end 4122 of the sealing element 412 contacts the clip 5 and fills the space between the clip 5 and the heated spiral tube 2. The length of the lower end 322 is about at or between 10 to 25 mm, providing sufficient area for a gripping portion 418 for the user. As shown in FIG. 10, specifically, the outer surface of the fourth end 4122 of the sealing element 412 can have at least one height difference, in the form of a groove or protrusion to facilitate user grip. The sealing element 412 can be made from materials with good sealing properties and capable of slight deformation, such as silicone or rubber with a hardness of at or between 30 and 70 Shore A, or thermoplastic elastomer with a hardness of at or between 20 and 80 Shore A.

Figure 11:
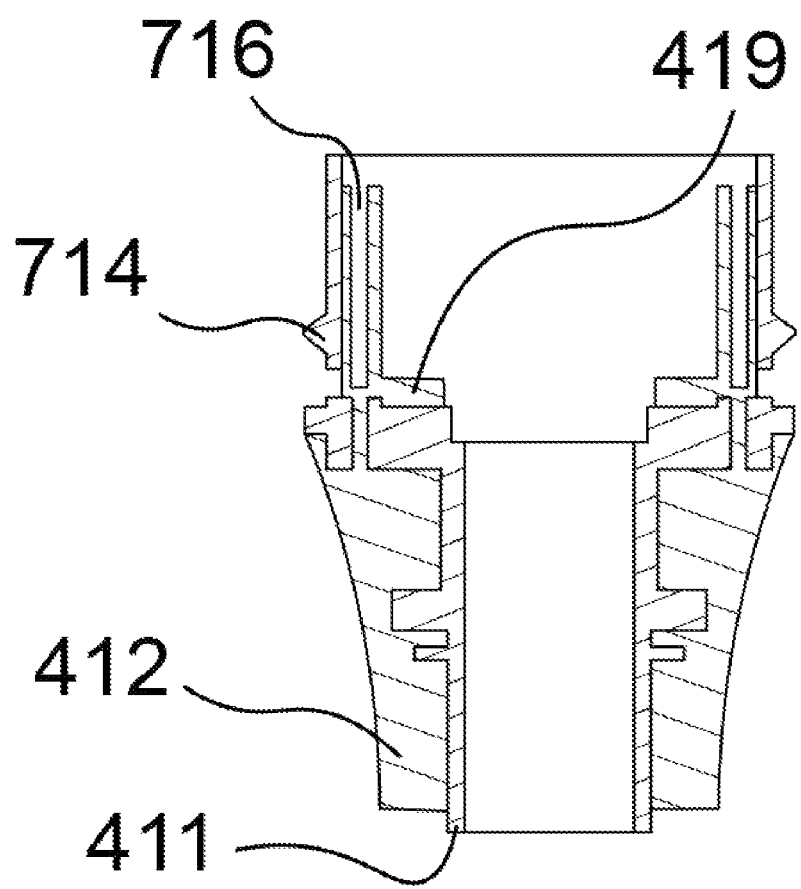
FIG. 11 is a schematic diagram of a sealing ring in accordance with an embodiment.

As shown in FIG. 11, specifically, a sealing ring 419 can be provided at both the patient interface end 3 and the airflow generator end 4. When the sealing ring 419 is placed between the contact area of the elbow and the patient interface end 3 or the contact area between the top end of the air delivery tube and the airflow generator end 4, a seal can be effectively achieved. When positioned at the bottom of the upper end 321 or between the third end 4121 and the fourth end 41122 of the sealing element 412 at the airflow generator end 4, the sealing ring 419 provides an elastic contact surface for the external intruding objects (an elbow or an air supply tube), creating a tighter seal and preventing gas leakage at the connection junction. Moreover, because the part in contact with the sealing ring 419 is made of rigid materials like plastic, placing the sealing ring 419 on the bottom of the upper end 321 helps maintain the sealing ring 419 in a correct position and the sealing ring 419 is less prone to movement or deformation. Besides, accidental loosening or loss of sealing properties of the sealing ring 419 can be avoided. Furthermore, the absence of space between the intruding object and the rigid material prevents noise resulting from airflow passing through.

Figures 9A, 9B, 9C:
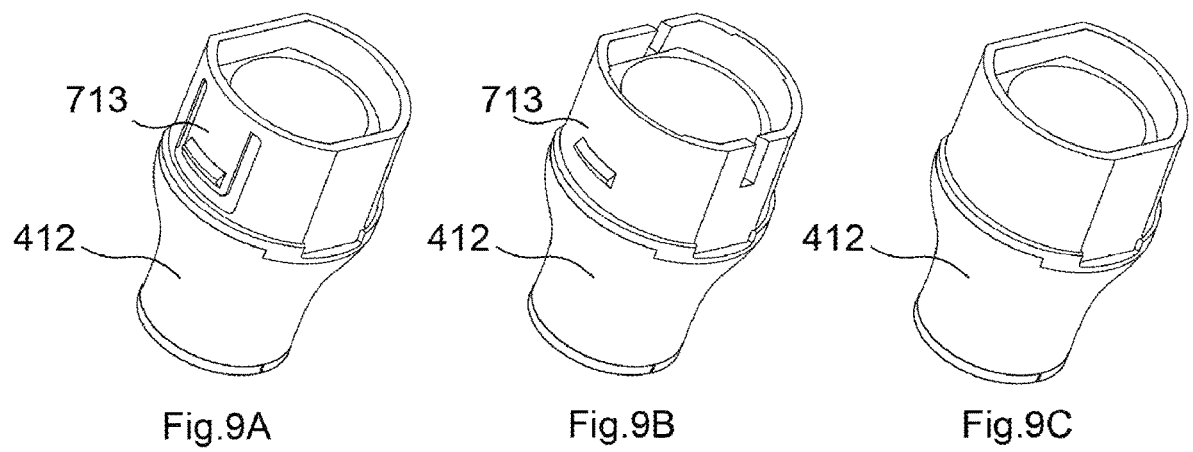
FIGS. 9A, 9B and 9C are structural schematic diagrams of different forms of a connecting clamp at the airflow generator end in accordance with an embodiment.

In another embodiment, as shown in FIG. 9B, specifically, the connecting clamp 713 at the airflow generator end 4 of the support element 411 may not have a gap 715. The connecting clamp 713 is made of a deformable material to snap-fit with the airflow generator, and the sealing element 412 corresponding to the position of the connecting clamp 713 may also have no clearance 716. As in FIG. 9C, there is no connecting clamp 713 at the airflow generator end 4; instead, the airflow generator end 4 directly connects to the air supply tube of the airflow generator through materials such as silicone, rubber, or thermoplastic elastomer.

Figure 12A:
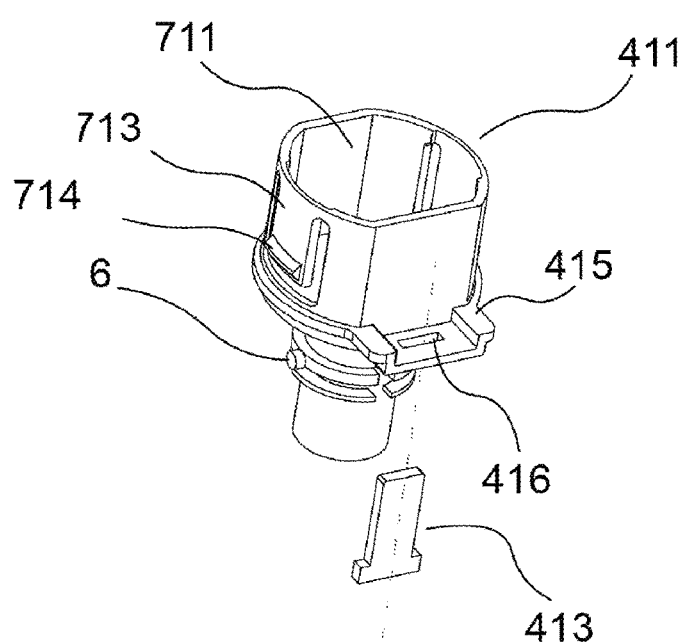
FIGS. 12A and 12B are schematic diagrams of the connection method between the electrical connector and the support element in accordance with an embodiment.
Figure 12B:
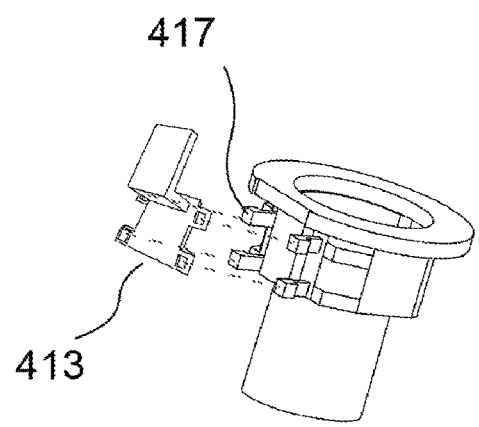
Figure 14A:
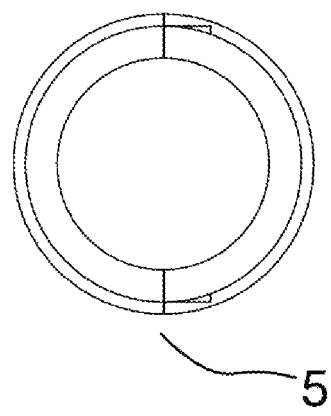
FIGS. 14A and 14B are schematic diagrams of the separated forms of a clip in accordance with an embodiment.
Figure 14B:
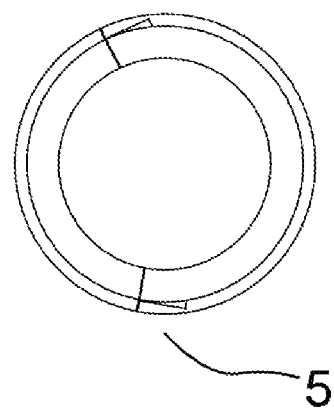

In another embodiment, as shown in FIG. 12, specifically, the electrical connector 413 has corresponding structures that match with a protrusion 417 or a groove on the support element 411 to connect to the support element 411, and then the connection is fixed in place by overmolding.

Embodiment 2

Figure 15C:
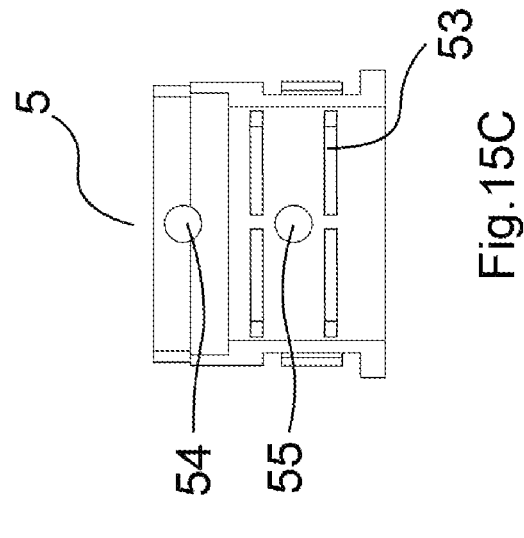
FIGS. 15A, 15B and 15C are schematic diagrams of the forms of a protruding piece of the clip in accordance with an embodiment.
Figure 15B:
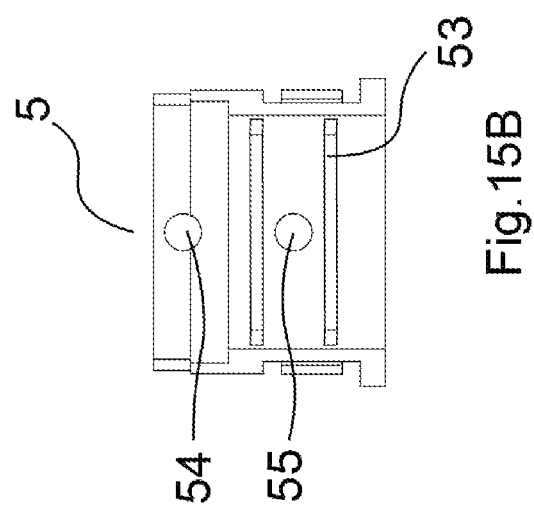
Figure 15A:
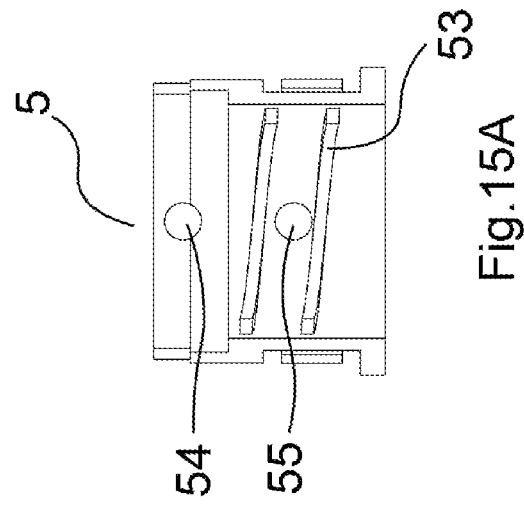
Figure 16A:
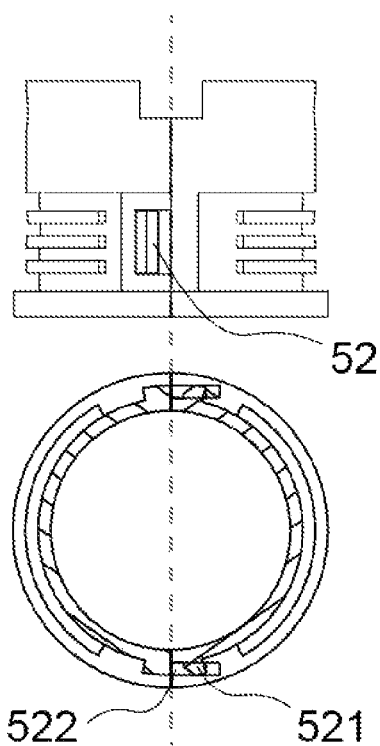
FIGS. 16A and 16B are schematic diagrams of the connection forms of a clip in accordance with an embodiment.
Figure 16B:
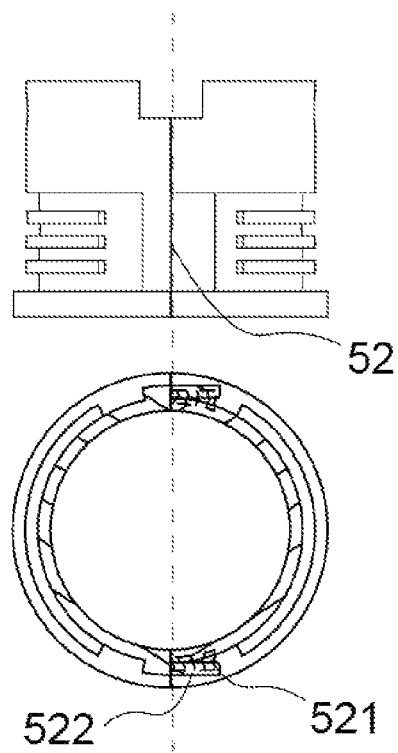

In this embodiment, a heatable air delivery tube 1 includes three parts: a patient interface end 3, an airflow generator end 4, and a heated spiral tube 2. The patient interface end 3 is configured to connect to an elbow or a short tube in the patient assembly, while the airflow generator end 4 is configured to connect to the air supply tube of the airflow generator, meaning the heated spiral tube 2 connects to the patient interface end 3 at one end and to the airflow generator end 4 at the other end. The air delivery tube 1 provided in this embodiment differs from the air delivery tube 1 in Embodiment 1 in that the structure of the clip 5 is specified. In this embodiment, the bracket 31 or the support element 411 makes direct contact with the heated spiral tube 2, and the wall of the bracket 31 has a positioner 6 configured to contact the clip 5. The clip 5 is fixed to the bracket 31 or the support element 411 by contacting the positioner 6, simultaneously, the heated spiral tube 2 is secured. As shown in FIG. 13, specifically, the clip 5 has an annular wall 51, which has a positioning receptacle 54 corresponding to the positioner 6 on the bracket 31 or the support element 411. The positioning receptacle 54 is configured to contact the positioner 6 and limit the movement of the clip 5; the annular wall 51 is externally configured to contact the elastomer 32 of the patient interface end 3 or the sealing element 412 of the airflow generator, and the exterior of the annular wall 51 is partially concave and convex to increase friction. As illustrated in FIG. 16, at least one connection is provided at the opening of the separated annular wall 51 in forms like a male-female buckle 52 (FIG. 16A), magnetic attraction (FIG. 16B), etc. When the connection form is a male-female buckle 52, the clip 5 has at least one pair of matching male buckle and female buckle. The inner circumference of the female buckle 522 is larger than the outer circumference of the male buckle 521, and the male buckle 521 has a slanted surface to guide the deformation of the female buckle 522. The annular wall 51 can be evenly divided in half or separated from one-third. The annular wall 51 has at least one through-opening serving as an inlet for the overmolding materials 55. As shown in FIG. 15, the annular wall 51 has an internal non-continuous protruding piece 53. After the clip 5 is connectable to the bracket 31 or the support element 411, the protruding piece 53 can extend into the space of the spiral thread of the heated spiral tube 2, forming a groove or platform 415 that limits displacement of the spiral tube. The protruding piece 53 may have a slope that complies with spiral threads or be flat, as shown in FIG. 15, FIG. 15A is a protruding piece 53 with a slope that complies with spiral threads, FIG. 15B and FIG. 15C are flat protruding pieces 53. The protruding length of the protruding piece 53 has a length of about at or between 1 to 5 mm to ensure the formed groove or the platform 415 is sufficient to prevent the heated spiral tube 2 from slipping. In another embodiment, the protruding piece 53 can also be continuous. As shown in FIG. 13A, the clip 5 has a separable annular wall 51 (two completely separated parts) and an anti-overflow surface 56, configured to contact the elastomer 32 of the patient interface end 3 or the sealing element 412 of the airflow generator, preventing downward overflow. The outer diameter of the anti-overflow surface 56 is greater than the outer diameter of the annular wall 51. The overall length of the clip 5 is about at or between 10 to 25 mm, with the minimum inner diameter of the annular wall 51 being no less than 11 mm to ensure the inside of the clip 5 can enclose the heated spiral tube 2, part of the bracket 31, or part of the support element 411. The clip 5 can be made from rigid materials such as polyethylene, polypropylene, polycarbonate, or from materials like silicone with a hardness above 40 Shore A, or thermoplastic elastomer materials with a hardness above 40 Shore A.

In another embodiment, to further enhance the convenience of product assembly and use, the clip 5 may also be configured without the male-female buckle 52 connection method. Instead, the clip 5 can rely on the deformation of the annular wall 51 snapping together with the internal protruding piece 53 to secure the spiral tube, or the clip 5 can utilize a mechanical clip structure for connection. As shown in FIG. 13B, part of the clip 5 connects to a structure that is not a male-female buckle, the separated form of the annular wall 51 can be one-piece with a connection (with at least one opening 416 that can be opened), and the connection form can be a plastic film connection, an inseparable hinge, etc. The clip 5 has a simple structure. By configuring the thickness of the annular wall 51, the clip 5 can deform. The clip 5 has an internal protruding piece 53 that secures the heated spiral tube 2. Once the bracket 31 or the support element 411 is connected to the heated spiral tube 2 and the clip 5, then they are overmolded to form a relatively stable end. As depicted in FIG. 13, the clip 5 employs a mechanical connection that allows the clip 5 to open and close on its own, making it more convenient and secure to use.

Embodiment 3

Figure 17:
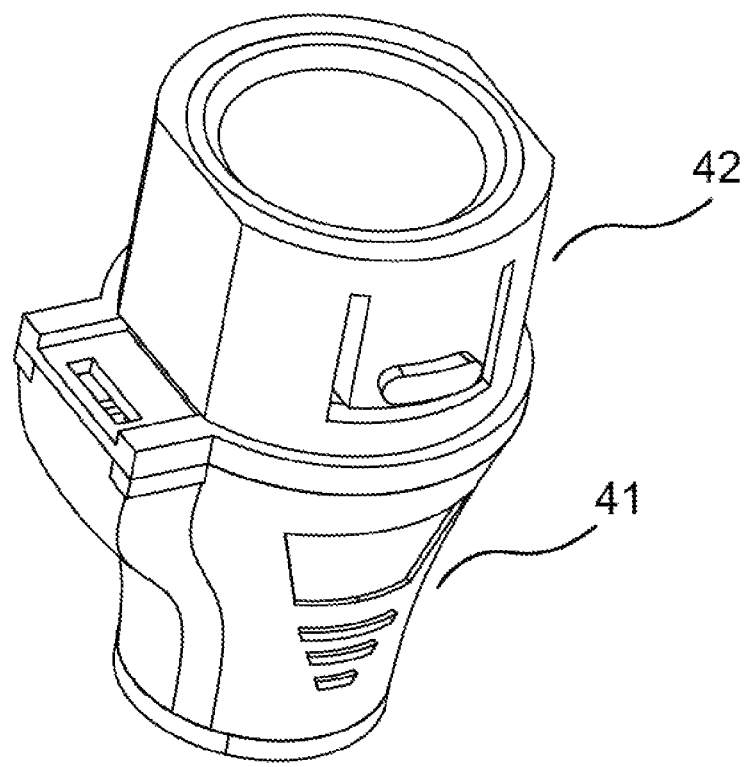
FIG. 17 is a structural schematic diagram of the modular airflow generator end in accordance with an embodiment.
Figure 18:
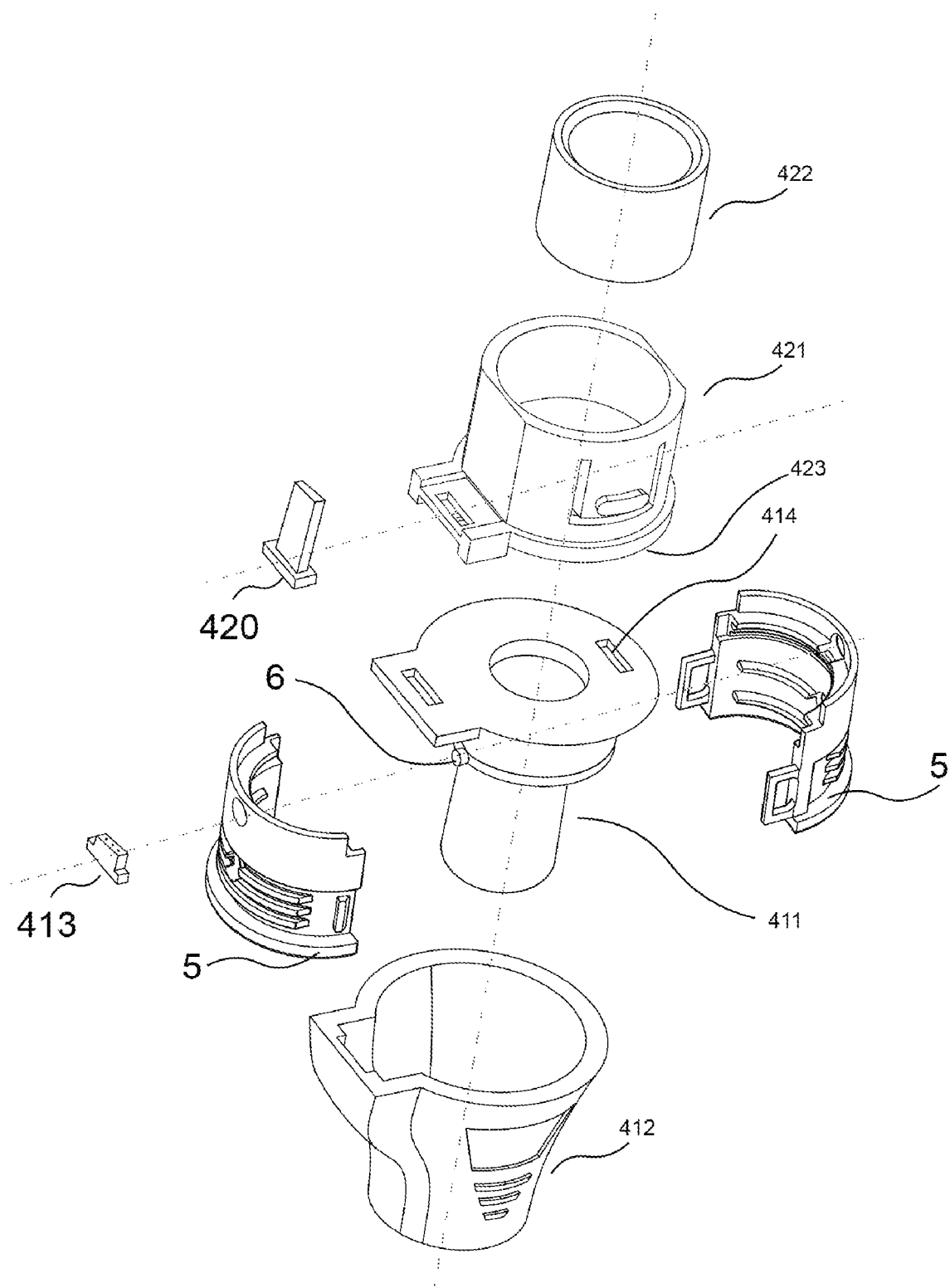
FIG. 18 is a structural exploded view of the modular airflow generator end in accordance with an embodiment.
Figure 19A:
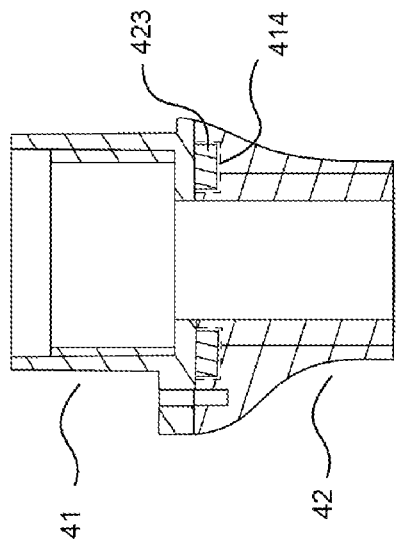
FIGS. 19A, 19B and 19C are schematic diagrams of the connection method of the modular airflow generator end in accordance with an embodiment.
Figure 19B:
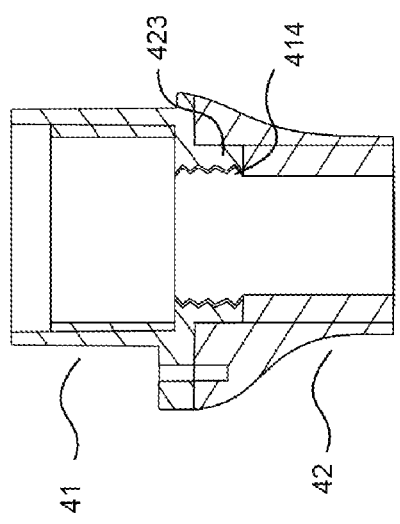
Figure 19C:
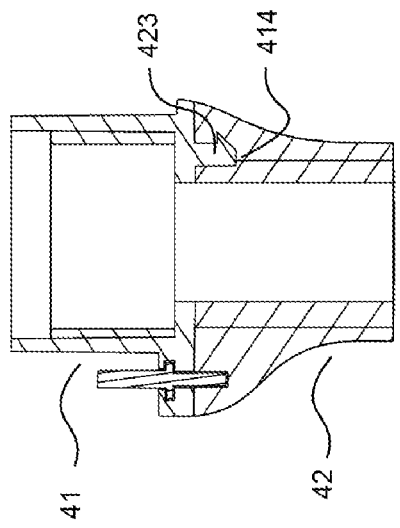

In this embodiment, a heatable air delivery tube 1 includes three parts: a patient interface end 3, an airflow generator end 4, and a heated spiral tube 2. The patient interface end 3 is configured to connect to an elbow or a short tube in the patient assembly, and the airflow generator end 4 is configured to connect to the air supply tube of the airflow generator. This means the heated spiral tube 2 is configured to connect to the patient interface end 3 at one end and to the airflow generator end 4 at the other end. The air delivery tube 1 provided in this embodiment is distinct from that in Embodiment 1 in that it specifies a modular form for the airflow generator end 4. As illustrated in FIG. 17 and FIG. 18, specifically, the airflow generator end 4 of the air delivery tube 1 includes a first part 41 that connects to the heated spiral tube 2 and a second part 42 that connects to the first part 41. The first part 41 and the second part 42 can be modularly connected and disconnected through a connecting portion 414 and a corresponding portion 423. In other words, different first parts 41 can be combined with different second parts 42 in a detachable or undetachable manner, provided that the connecting portion 414 and the corresponding portion 423 are structurally matched. As shown in FIG. 19, the connecting portion 414 and the corresponding portion 423 (i.e., the first part 41 and the second part 42) can be in the form of snap-fit, magnetic attraction, rotation, ultrasonic, or other detachable or undetachable connection method (FIG. 19A shows a snap-fit type, FIG. 19B is a rotation type, and FIG. 19C displays a magnetic attraction type). The first part 41 includes a support element 411, a sealing element 412, a clip 5 to secure the heated spiral tube 2, a connecting portion 414, and an electrical connector 413. The support element 411 includes a wall that creates a cylinderical through-passage within its structure, with a minimum inner diameter of no less than 10 mm, ensuring the smooth passage of pressurized airflow. The support element 411 is configured to connect to the heated spiral tube 2 and the clip 5. Part of the support element 411 is connectable to the heated spiral tube 2 through the clip 5, and a positioner 6 in contact with the clip 5 is provided. The electrical connector 413 of the first part 41 forms a continuous circuit with the electrical connector 420 of the second part 42. The second part 42 includes a shell 421, soft rubber 422, a corresponding portion 423, and an electrical connector 420. The soft rubber 422 has a hollow section sized to accommodate and deformably fixed to the air supply tube of the airflow generator. As shown in FIG. 19, the first part 41 of the airflow generator end 4 connects to the heated spiral tube 2 and serves as a base, while the second part 42 can have different forms based on requirements. By replacing the second part 42, the air delivery tube 1 can be modularized, which simplifies the production and development processes. The overall length of the first part 41 is about at or between 10 to 30 mm, ensuring sufficient contact surface for the support element 411 with the heated spiral tube 2 and the clip 5, as well as providing a gripping portion for the user. The total length of the second part 42 is about at or between 10 to 30 mm, ensuring the second part 42 can house the air supply tube of the airflow generator. The support element 411 of the first part 41 and the shell 421 of the second part 42 can be made from the same or different materials. And the sealing element 412 of the first part 41 and the sealing element 412 of the second part 42 can also be made from the same or different materials. As shown in FIG. 19, the connection method between the electrical connector 413 of the first part 41 and the electrical connector 420 of the second part 42 can be slot-type or contact-type. The slot of the slot-type can be rectangular, square, or circular. When the connection method between the first part 41 and the second part 42 is slot-type, the connecting portion 414 employs forms such as snap-fit (as shown in FIG. 19A), magnetic attraction, and others. When the connection method is contact-type, the connecting portion 414 utilizes forms such as rotation (as shown in FIG. 19B), magnetic attraction (as shown in FIG. 19C), and others.

In another embodiment, as illustrated in FIG. 9B, specifically, the support element 411 provided on the connecting clamp 713 at the airflow generator end 4 can have no gap 715. By using a connecting clamp 713 made from deformable material, the connecting clamp 713 can snap-fit with the airflow generator. The sealing element 412 corresponding to the position of the connecting clamp 713 can also have no clearance 716. As shown in FIG. 9C, the airflow generator end 4 without the connecting clamp 713 is configured to directly connect to the air supply tube of the airflow generator through materials such as silicone, rubber, or thermoplastic elastomer.

Embodiment 4

Figure 20:
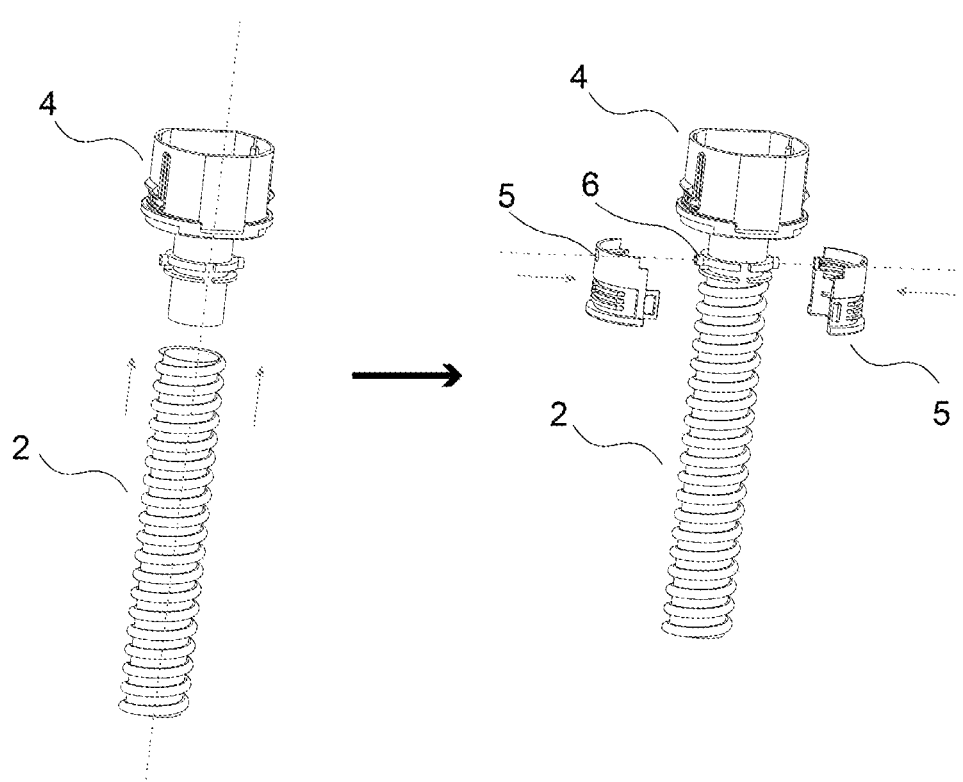
FIG. 20 is a schematic diagram of the assembly of a heated spiral tube and the clip in accordance with an embodiment.

In this embodiment, a heatable air delivery tube 1 includes three parts: a patient interface end 3, an airflow generator end 4, and a heated spiral tube 2. The patient interface end 3 is configured to connect to either an elbow or a short pipe within the patient component, while the airflow generator end 4 is configured to connect to the air supply tube of the airflow generator. This means that the heated spiral tube 2 is configured to connect to the patient interface end 3 at one end, and to the airflow generator end 4 at the other end. As shown in FIG. 20 (which only displays the connection method for the airflow generator end, as the connection method for the patient interface end and the airflow generator end are the same), specifically, this embodiment provides a method of connecting the airflow generator end 4 of the air delivery tube 1 with the heated spiral tube 2. For the airflow generator end 4, a heated spiral tube 2 with metal wires, a support element 411 of the airflow generator end 4, an electrical connector 413, a silicone ring (in some embodiments, no silicone ring is required), and a clip 5 need to be prepared. Then the steps are as follows: 1) Slide the other end of the heated spiral tube 2 onto the part of the support element 411 that is provided to contact the heated spiral tube 2. 2) Fit the electrical connector 413 with a silicone ring. 3) Insert the electrical connector 413 into the support element 411, and the silicone ring secures the electrical connector 413. 4) Open the clip 5 and then snap the clip 5 closed to secure the heated spiral tube 2 between the support element 411 and the clip 5. 5) Proceed with overmolding. For the patient interface end 3, a heated spiral tube 2 with metal wires, a bracket 31 of the patient interface end 3, a thermistor 33, and a clip 5 need to be prepared. The steps are: 1) Slide one end of the heated spiral tube 2 onto the part of the bracket 31 that is provided to contact the heated spiral tube 2. 2) Place the thermistor 33 into the cavity 311 of the bracket 31. 3) Open the clip 5 and then snap the clip 5 closed to secure the heated spiral tube 2 between the bracket 31 and the clip 5. 4) Proceed with overmolding.

In another embodiment, the bracket 31 of the patient interface end 3 or the support element 411 of the airflow generator end 4 may not have a positioner 6. The clip 5 directly clamps the heated spiral tube and then the overmolding process is performed.

In yet another embodiment, the connection between the heated spiral tube and the patient interface end or airflow generator end may not involve the clip 5.

Furthermore, it is also possible to combine the technical features from the embodiments mentioned above as needed to obtain an air delivery tube 1 that includes all or some of the aforementioned technical features.

The benefits of a heatable air delivery tube provided by the disclosure can at least include:

1) The heatable air delivery tube provided by this disclosure incorporates a notch design. On the market, the end of most air delivery tubes that connect to an elbow usually has an inner diameter slightly larger than the outer diameter of the elbow. This design aims to ensure that the elbow can smoothly connect to the air delivery tube. The end that connects to the elbow, considering its need for sealability and tactile feel, is typically made from flexible materials like silicone, rubber, or thermoplastic elastomers. However, due to the frequent installation and removal required by the device, the flexible materials are prone to fatigue deformation or material aging from repeated stress loading and unloading. This results in a gradual loss of their original shape and elasticity, eventually leading to a failure of the sealing effect and an increased likelihood of slippage. To maintain the function of a smooth connection between the elbow and the air delivery tube and to extend the lifespan of the end that connects to the elbow, a notch is set at the upper end of the elastomer of the patient interface end. Additionally, the inner diameter of the elastomer is configured to be less than or equal to the outer diameter of the tube openings connected with the elastomer. a) The notch at the upper end of the elastomer provides a flexible structure, increasing the operability and adaptability of the elastomer. The upper end of the elastomer can be supported to deform into a broader aperture at the notch, allowing the lower end of the elbow or other tube openings to enter smoothly. b) The inner diameter of the elastomer being less than or equal to the outer diameter of the tube openings connected with the elastomer provides a tighter seal. Meanwhile, when the elastomer undergoes fatigue deformation, an elastomer with an inner diameter slightly larger than the outer diameter of the elbow will have an extended lifespan and avoid loosening after aging.

2) The heatable air delivery tube provided by this disclosure has a modular design for the airflow generator end. There are many well-known ventilators on the market, and different brands of ventilators have variations in their components. For the end of the air delivery tube that connects to the elbow, due to regulatory requirements, most on the market have connectors with a diameter of 15 mm or 22 mm. However, for the end that connects to the airflow generator, there are differences due to the brands' machine designs, making it difficult to achieve a universal design for the components. The modular design of the airflow generator end of the air delivery tube: the part that connects to the heated spiral tube only needs to meet the requirement of connecting to the heated spiral tube, so this part is configured as a universal base (a first part). The part that connects to different machines only needs to have a shape that is compatible with the machine and have positions for placing the electrical connectors. The base and the changeable upper part (a second part) can be connected through simple methods like snap-fit, rotation, ultrasonic, etc. Electrical connectors, can form a continuous circuit through slot-type or contact-type connections. When the base and the changeable upper part are configured separately, the base's fixed connection with the heated spiral tube is more complex compared to the upper part's connection with the machine. With a universal base, the upper part model that connects to the machine can be configured and manufactured more simply. By changing the adaptability of the upper part, the effect of matching different machine models can be achieved. This modular design provides at least three benefits: a) For manufacturing and design, modular design reduces the burden of production and assembly, improves the product's customizability which means that with a universal base, the upper part can be configured to match different machines and meet the needs of different machines as a whole. This design also helps speed up development and production, and reduces costs and the repetition of design and manufacturing work by mass-producing the same base part. Moreover, such a feature focuses on controlling modular components rather than the whole during production, further reducing the overall scrap rate, and saving production costs. b) For product quality, modular design supports individual testing and verification, improving quality control, and enables the introduction of new technologies by replacing or upgrading individual modules, allowing gradual upgrades to meet or adapt to new technologies or standards without affecting the overall system. c) For storage costs, modular design reduces the overall number of products in storage, requiring only the storage of necessary modules or components. In this way, the warehouse space can be more effectively utilized and the corresponding module inventory can be adjusted according to market demand, reducing the occurrence of insufficient inventory or overpurchasing and backlog due to fluctuations in demand. d) For the environment, air delivery tubes typically contain plastic materials like polyethylene and polycarbonate, whose production involves the use of fossil fuels, consuming large amounts of oil and natural gas, non-renewable resources, and emitting greenhouse gases. After use, plastic products are not easily degradable and can accumulate in the environment, causing pollution. Modular design improves the overall flexibility of the product, and during the maintenance process, only the relevant module parts rather than the entire product need to be replaced. This not only reduces maintenance costs but also allows damaged modules to be recycled or upgraded for research, reducing waste, resource consumption, and energy use, making it more environmentally friendly.

3) The heatable air delivery tube provided by this disclosure includes a universal design for the clip. The air delivery tube 1 includes two connection junctions with the heated spiral tube 2, where the heated spiral tube 2 is secured at both ends using the clip 5 and then overmolded. This ensures a more stable connection and extends the overall lifespan of the tube. Since the functions realized by the two ends of the air delivery tube when connected to other external components are different, their structural designs also slightly vary. However, the part that connects to the heated spiral tube can be configured to be substantially the same, achieving a universal design for the clip. The extensive use of the clip in a product contributes to reducing research and development costs as well as production costs. The research and development phase can be as simple as designing and verifying that the connection at one end is reasonable and stable, reducing the additional costs associated with constant modification and customization.

4) The heatable air delivery tube provided by this disclosure has a unique connection method of the heated spiral tube. To ensure the stability of the connection between the heated spiral tube and the airflow generator end and the patient interface end, the connection between the heated spiral tube and the two ends is achieved through a clip. Firstly, the parts at both ends that contact the heated spiral tube have a positioner and a sufficient contact surface in contact with the heated spiral tube. The positioner provides positioning for the clip to prevent it from moving, and the sufficient contact surface provides a force area for the heated spiral tube, increasing friction between the heated spiral tube and the two ends. Secondly, the clip has a positioning receptacle and an internal protruding piece. The positioning receptacle works with the positioner at both ends, and the internal protruding piece intrudes into the space of the spiral tube, limiting displacement of the heated spiral tube. This setup achieves the first fixation among the heated spiral tube, the airflow generator end and the patient interface end. Finally, by molding, materials like silicone with good deformation capability are injected into the space between the heated spiral tube, the airflow generator end and the patient interface end, enhancing the friction in the connection and achieving a second fixation, ultimately better securing the whole assembly.

5) The heatable air delivery tube provided by this disclosure has a specifically designed connecting clamp at the airflow generator end. The connection to the airflow generator is mechanically fixed. To achieve user-friendliness, the wall thickness of the connecting clamp is configured to be no greater than the wall thickness of other parts, allowing the connecting clamp to have elastic arms that can deform. A guiding slanted surface is set on the connecting clamp, enabling the airflow generator end to autonomously deform upon entering the connection port of the machine and to secure to the airflow generator. Simultaneously, the reverse slanted surface guides the elastic arms to deform for separation, making the product easier for users to handle.

6) The heatable air delivery tube provided by this disclosure presents a recessed design of the sealing element of the airflow generator end. Due to the inflexibility in size of the machine and the specificity of the user group, connecting the airflow generator end can be challenging because of the blind spot in the field of vision, making it difficult for the user to locate the interface between the end and the machine. By designing the interior of the connection junction to be recessed, creating a height difference with the end surface of the connection junction to form a groove, this allows the product to have a positioning function when it interfaces with the machine through the groove, aiding the particular user group in achieving easier connections.

The embodiments described above merely represent several implementations of the disclosure. While the descriptions are specific and detailed, they should not be understood as limiting the scope of the disclosure. It should be noted that for those of ordinal skills in the field, several modifications and improvements can be made without departing from the concept of the disclosure, and these are also considered within the scope of the disclosure. Therefore, the protection scope of the disclosure should be determined by the appended claims.

It must be noted that as used herein and in the appended claims, the singular forms "a", "an", and "the" include their plural equivalents, unless the context clearly dictates otherwise.

The invention claimed is:

1. A heatable air delivery tube, configured to form a connection with an airflow generator and a patient interface assembly, and to deliver pressurized breathable gas to an airway of a patient, the air delivery tube comprising:
   an airflow generator end, which includes a support element, a sealing element, a first clip, and an electrical connector,
   wherein the support element and the sealing element are configured to be partially in contact with the airflow generator, and the support element is configured to be interconnected to the sealing element,
   wherein the first clip is configured to secure a heated spiral tube, the electrical connector is configured to connect to the airflow generator to form a continuous circuit,
   wherein the support element includes a first end and a second end, and the first end is configured to be internally connectable to the sealing element and includes a connecting clamp, wherein the connecting clamp includes a gap and a guiding slanted protrusion, and is configured to be deformably fixed to the airflow generator,
   wherein the second end is configured to be externally connectable to the heated spiral tube and the first clip, and the second end includes a positioner in contact with the first clip,
   wherein the sealing element includes a third end and a fourth end, with the third end including a clearance at a position corresponding to the connecting clamp, and having an inner diameter not exceeding an outer diameter of an air supply tube of the airflow generator, and wherein the third end is configured to seal the airflow generator, while the fourth end is configured to provide a gripping portion;
   the heated spiral tube, configured to connect to a patient interface end at one end and to the airflow generator end at an other end, including metal wires, a compressible flexible wall, and a spring-like coil, together to form the compressible heated spiral tube; and
   the patient interface end, configured to connect to the heated spiral tube, including an elastomer to connect to the patient interface assembly, a bracket to connect to the heated spiral tube, and a second clip to secure the heated spiral tube.

2. The heatable air delivery tube according to claim 1, wherein the third end of the sealing element of the airflow generator end is configured to be partially recessed to form a height difference or a groove with a surface of the first end of the support element.

3. The heatable air delivery tube according to claim 1, wherein a sealing ring is provided between the third end and the fourth end of the sealing element of the airflow generator end.

4. The heatable air delivery tube according to claim 1, wherein a gripping portion is provided on the fourth end of the sealing element of the airflow generator end, with the gripping portion being configured to form a height difference with a surface of the fourth end.

5. The heatable air delivery tube according to claim 1, wherein the support element at the airflow generator end includes an opening to accommodate the electrical connector, with the opening being surrounded by a channel to house a silicone ring, and the electrical connector being larger than the opening.

6. The heatable air delivery tube according to claim 1, wherein the first clip includes an annular wall, and a separable form of the annular wall is either a one-piece with a connection or two completely separated parts, with the annular wall being evenly divided in half or being separated from a one-third point.

7. The heatable air delivery tube according to claim 6, wherein an internal protruding piece provided on the annular wall of the first clip is non-continuous, either provided with a slope that complies with spiral threads or being flat, and wherein an exterior of the annular wall of the first clip is partially concave and convex, with the annular wall including at least one inlet for overmolding materials.

8. A heatable air delivery tube, configured to form a connection with an airflow generator and a patient interface assembly, and to deliver pressurized breathable gas to an airway of a patient, the air delivery tube comprising:
   a patient interface end, configured to connect to a heated spiral tube, including an elastomer to connect to the patient interface assembly, a bracket to connect to the heated spiral tube, and a first clip to secure the heated spiral tube, wherein the bracket includes a positioner;
   an airflow generator end, configured to connect to the heated spiral tube, including a sealing element to be in contact with the airflow generator, a support element to position the airflow generator, a second clip to secure the heated spiral tube, and an electrical connector, wherein the support element includes another positioner;
   the heated spiral tube, configured to connect to the patient interface end at one end and to the airflow generator end at an other end, including metal wires, a compressible flexible wall, and a spring-like coil, together to form the compressible heated spiral tube;
   the first clip, including a separable annular wall, at least one pair of matching male buckle and female buckle, an anti-overflow surface, a positioning receptacle, with the annular wall being externally configured to contact the elastomer of the patient interface end or the sealing element of the airflow generator, and the annular wall including an internal protruding piece that is configured to limit displacement of the heated spiral tube, and
   wherein the male buckle includes a slanted surface to guide deformation of the female buckle, an inner edge circumference of the female buckle is larger than an outer edge circumference of the male buckle, and the positioning receptacle includes a form corresponding to the positioner, which is configured to contact and limit movement of the first clip.

9. The heatable air delivery tube according to claim 8, wherein the anti-overflow surface has an outer diameter greater than an outer diameter of the annular wall, which is configured to contact and prevent downward overflow of the elastomer of the patient interface end or the sealing element of the airflow generator.

10. The heatable air delivery tube according to claim 8, wherein a separable form of the annular wall of the first clip is either a one-piece with a connection or two completely separated parts, with the annular wall being evenly divided in half or being separated from a one-third point.

11. The heatable air delivery tube according to claim 8, wherein the protruding piece of the annular wall of the first clip is non-continuous, either provided with a slope that complies with spiral threads or being flat.

12. The heatable air delivery tube according to claim 8, wherein an exterior of the annular wall of the first clip is partially concave and convex, and the annular wall includes at least one inlet for overmolding materials.

13. A heatable air delivery tube, configured to form a connection with an airflow generator and a patient interface assembly, and to deliver pressurized breathable gas to an airway of a patient, the air delivery tube comprising:
   a patient interface end, configured to connect to a heated spiral tube, including an elastomer to connect to the patient interface assembly, a bracket to connect to the heated spiral tube, and a first clip to secure the heated spiral tube; and
   an airflow generator end, including a first part connectable to the heated spiral tube and a second part connectable to the first part, wherein the second part is configured to seal the airflow generator,
   wherein the first part includes a support element, a sealing element, a second clip, a connecting portion, and an electrical connector, with the second clip being configured to secure the heated spiral tube, the electrical connector configured to connect to an electrical connector of the second part to form a continuous circuit,
   wherein the support element is configured to connect to the heated spiral tube and the second clip, and includes a positioner in contact with the second clip,
   wherein the second part is deformably fixed to the airflow generator, including a shell, a soft rubber, a corresponding portion, and the electrical connector,
   wherein the soft rubber includes a hollow section to accommodate an air supply tube of the airflow generator, wherein the electrical connector of the second part connects to the electrical connector of the first part to form a continuous circuit,
   wherein the first part and the second part are connectable through the connecting portion and the corresponding portion, and
   wherein the heated spiral tube, configured to connect to the patient interface end at one end and to the airflow generator end at the other end, including metal wires, a compressible flexible wall, and a spring-like coil, together to form the compressible heated spiral tube.

14. The heatable air delivery tube according to claim 13, wherein the first part and the second part of the airflow generator are connectable by one or more detachable or undetachable methods: snap-fitting, magnetic attraction, rotation, or ultrasonic.

15. The heatable air delivery tube according to claim 13, wherein the second part of the airflow generator is provided with different forms as needed.

16. The heatable air delivery tube according to claim 13, wherein the electrical connector of the first part and the electrical connector of the second part are either slot-type or contact-type.

17. The heatable air delivery tube according to claim 13, wherein the sealing element of the airflow generator end further includes a third end and a fourth end, with the third end of the sealing element being partially recessed to form a height difference or a groove with a surface of a first end of the support element.

\* \* \* \* \*